US008796235B2

(12) United States Patent
Mohapatra et al.

(10) Patent No.: US 8,796,235 B2
(45) Date of Patent: Aug. 5, 2014

(54) METHODS FOR ATTENUATING DENGUE VIRUS INFECTION

(75) Inventors: Shyam S. Mohapatra, Tampa, FL (US); Weidong Zhang, Tampa, FL (US)

(73) Assignee: University of South Florida, Tampa, FL (US)

( * ) Notice: Subject to any disclaimer, the term of this patent is extended or adjusted under 35 U.S.C. 154(b) by 643 days.

(21) Appl. No.: 10/544,146

(22) PCT Filed: Feb. 23, 2004

(86) PCT No.: PCT/US2004/005566
§ 371 (c)(1),
(2), (4) Date: May 5, 2006

(87) PCT Pub. No.: WO2004/076664
PCT Pub. Date: Sep. 10, 2004

(65) Prior Publication Data
US 2006/0239971 A1    Oct. 26, 2006

Related U.S. Application Data

(60) Provisional application No. 60/320,108, filed on Apr. 15, 2003, provisional application No. 60/319,964, filed on Feb. 21, 2003.

(51) Int. Cl.
| | |
|---|---|
| C12N 15/11 | (2006.01) |
| C12N 15/00 | (2006.01) |
| C12N 15/86 | (2006.01) |
| C12N 7/00 | (2006.01) |
| A61K 39/12 | (2006.01) |

(52) U.S. Cl.
USPC ....... 514/44 A; 435/320.1; 435/455; 435/456; 435/235.1; 435/218.1; 435/488

(58) Field of Classification Search
None
See application file for complete search history.

(56) References Cited

U.S. PATENT DOCUMENTS

| | | | |
|---|---|---|---|
| 5,290,540 A | | 3/1994 | Prince et al. |
| 5,693,532 A | | 12/1997 | McSwiggen et al. |
| 5,831,069 A | | 11/1998 | Barik |
| 5,998,602 A | | 12/1999 | Torrence et al. |
| 6,136,597 A | * | 10/2000 | Hope et al. ..................... 435/325 |
| 6,391,318 B1 | | 5/2002 | Illum et al. |
| 6,489,306 B2 | | 12/2002 | Mohapatra et al. |
| 6,586,579 B1 | | 7/2003 | Huang et al. |
| 6,852,528 B2 | * | 2/2005 | Yu et al. ..................... 435/320.1 |
| 6,900,299 B1 | | 5/2005 | Mohapatra et al. |
| 7,056,704 B2 | * | 6/2006 | Tuschl et al. ................. 435/91.1 |
| 7,067,633 B2 | * | 6/2006 | Kumar et al. ................. 530/350 |
| 7,118,888 B2 | | 10/2006 | Mohapatra et al. |
| 7,297,786 B2 | | 11/2007 | McCray et al. |
| 7,354,908 B2 | | 4/2008 | Mohapatra et al. |
| 7,425,618 B2 | | 9/2008 | Oliver et al. |
| 7,595,303 B1 | | 9/2009 | Mohapatra et al. |
| 7,655,772 B2 | | 2/2010 | Mohapatra |
| 2001/0006951 A1 | | 7/2001 | Mohapatra et al. |
| 2002/0173478 A1 | | 11/2002 | Gewirtz |
| 2003/0068333 A1 | | 4/2003 | Mohapatra et al. |
| 2003/0139363 A1 | | 7/2003 | Kay et al. |
| 2003/0143732 A1 | | 7/2003 | Fosnaugh et al. |
| 2003/0148519 A1 | | 8/2003 | Engelke et al. |
| 2003/0157691 A1 | | 8/2003 | Qin et al. |
| 2003/0166282 A1 | | 9/2003 | Brown et al. |
| 2003/0170891 A1 | | 9/2003 | McSwiggen |
| 2003/0175772 A1 | | 9/2003 | Wang |
| 2003/0175950 A1 | | 9/2003 | McSwiggen |
| 2003/0190635 A1 | | 10/2003 | McSwiggen |
| 2003/0198624 A1 | | 10/2003 | Mohapatra et al. |
| 2004/0002077 A1 | | 1/2004 | Taira et al. |
| 2004/0002458 A1 | | 1/2004 | Seilhamer et al. |
| 2004/0009152 A1 | | 1/2004 | Mohapatra et al. |
| 2004/0018176 A1 | | 1/2004 | Tolentino et al. |
| 2004/0019001 A1 | | 1/2004 | McSwiggen |
| 2004/0023390 A1 | | 2/2004 | Davidson et al. |
| 2004/0029275 A1 | | 2/2004 | Brown et al. |
| 2004/0137471 A1 | | 7/2004 | Vickers et al. |
| 2004/0175384 A1 | | 9/2004 | Mohapatra et al. |
| 2004/0242518 A1 | | 12/2004 | Chen et al. |
| 2004/0259247 A1 | | 12/2004 | Tuschl et al. |
| 2005/0096291 A1 | * | 5/2005 | Iversen et al. ................... 514/44 |

(Continued)

FOREIGN PATENT DOCUMENTS

| | | |
|---|---|---|
| WO | WO 03/028759 A1 | 4/2003 |
| WO | WO 03/070918 A2 | 8/2003 |

(Continued)

OTHER PUBLICATIONS

Paddison et al (PNAS 99(3): 1443-1448, 2002).*

(Continued)

Primary Examiner — Richard Schnizer
(74) Attorney, Agent, or Firm — Saliwanchik, Lloyd & Eisenschenk

(57) ABSTRACT

The present invention pertains to vectors for regulating gene expression having at least one gene expressing cassette and at least one gene suppressing cassette, wherein the gene expression cassette encodes a polypeptide of interest, and wherein the gene suppressing cassette encodes a short interfering RNA (siRNA) molecule that reduces expression of a target gene by RNA interference. The present invention further includes vectors that contain suppressor cassettes in conjunction with cassettes upregulating gene expression regulated by either a constitutive promoter, such as a general CMV promoter, or a tissue specific promoter. The present invention further includes vectors that contain Dengue virus gene suppression cassettes. The present invention further includes pharmaceutical compositions containing such vectors, methods of modulating the expression of genes in a host using such vectors, and method of producing such vectors.

8 Claims, 10 Drawing Sheets

(56) References Cited

U.S. PATENT DOCUMENTS

| | | | |
|---|---|---|---|
| 2005/0106598 A1 | 5/2005 | Manoharan et al. | |
| 2005/0158327 A1 | 7/2005 | Mohapatra et al. | |
| 2005/0159385 A1 | 7/2005 | Mohapatra | |
| 2005/0266093 A1 | 12/2005 | Mohapatra | |
| 2005/0272650 A1 | 12/2005 | Mohapatra | |
| 2006/0068405 A1 | 3/2006 | Diber et al. | |
| 2006/0276382 A1 | 12/2006 | Mohapatra | |
| 2007/0009951 A1 | 1/2007 | Mohapatra et al. | |
| 2007/0031844 A1* | 2/2007 | Khvorova et al. | 435/6 |
| 2007/0116767 A1 | 5/2007 | Mohapatra | |
| 2007/0265204 A1 | 11/2007 | Mohapatra et al. | |
| 2008/0023325 A1 | 1/2008 | Mohapatra et al. | |
| 2008/0070858 A1 | 3/2008 | Mohapatra | |
| 2008/0075731 A1 | 3/2008 | Mohapatra et al. | |
| 2008/0100279 A1 | 5/2008 | Mohapatra et al. | |
| 2008/0249057 A1 | 10/2008 | Mohapatra et al. | |
| 2009/0280143 A1 | 11/2009 | Mohapatra et al. | |

FOREIGN PATENT DOCUMENTS

| | | |
|---|---|---|
| WO | WO 03/092618 A2 | 11/2003 |
| WO | WO 2004/074314 A2 | 8/2004 |
| WO | WO 2004/076664 A2 | 9/2004 |
| WO | WO 2005/056021 A1 | 6/2005 |
| WO | WO 2005/094420 A2 | 10/2005 |
| WO | WO 2005/105136 A1 | 11/2005 |
| WO | WO 2007/127480 A2 | 11/2007 |
| WO | WO 2007/127487 A2 | 11/2007 |

OTHER PUBLICATIONS

Adelman et al (Insect Mol. Biol. 10(3): 265-273, 2001).*
Adelman et al (J. Virol. 76(24): 12925-12933, 2002).*
Jessie et al (J. Inf. Dis. 189: 1411-1418, 2004).*
Verma et al (Nature 389: 239-242, 1997).*
Anderson (Nature 392:25-30, 1998).*
Romano et al (Stem Cells 18: 19-39, 2000).*
Somia and Verma (Nature Reviews Genetics 1: 91-99, 2000).*
Rosenberg et al (Science 287 :1751, 2000).*
Caplen 2003, Expert Opin. Biol. Ther. 2003, vol. 3, pp. 575-586.*
Raviprakash et al (J. Virol. 69(1):69-74, 1995).*
Yu et al (PNAS 99(9): 6047-6052, 2002).*
Halstead (Vaccine 23: 849-856, 2005).*
An et al (Virology 263: 70-77, 1999).*
Liu et al (Gene Therapy 6 : 1258-1266, 1999).*
Coburn (J. Antimicro. Chemo. 51: 753-756, 2003).*
Lieberman (Trends Mol. Med 9(9): 397-403, 2003).*
Libraty et al ( J. Virol 75(8): 3501-3508, 2001).*
Palmowski et al (J. Immunol. 172: 1582-1587, 2004).*
Condon et al (Nature Medicine 2(10): 1122-1128, 1996).*
Song et al (Proc. Nat. Acad. Sci. USA 94: 1943-1948, 1997).*
Porgador et al (J. Exp. Med. 188(6): 1075-1082, 1998).*
Barratt-Boyes (J. Immunol. 164: 2487-2495, 2000).*
Larregina et al (Gene Therapy 8: 608-617, 2001).*
McCaffrey et al (Nature 418 : 38-39, 2002).*
Huong et al (J. Virol. Methods 95: 19-32, 2001).*
U.S. Appl. No. 10/544,145, filed Aug. 2, 2005, Mohapatra et al.
U.S. Appl. No. 10/581,580, filed Jun. 2, 2006, Mohapatra et al.
U.S. Appl. No. 10/655,873, filed Sep. 5, 2003, Mohapatra et al.
Adelman, Z.N. of el. "RNA silencing of dengue virus type 2 replication in transformed C6/36 mosquito cells transcribing an inverted-repeat RNA derived from the virus genome" *J. Virology*, 2002, 76:12925-12933.
Adelman, Z.N. et al. "Sindbis virus-induced silencing of derigue viruses in mosquitoes" *Insect Mol Biol.*, 2001, 10:265-273.
Abbas-Terki, T. et al. "Lentiviral-mediated RNA interference" *Human Gene Therapy*, 2002, 13:2197-2201.
Banchereau, J. and Steinman, R.M. "Dendritic cells and the control of immunity" *Nature*, 1998, 392:245-252.
Blair, C.D. et al. "Molecular strategies for interrupting arthropod-borne virus transmission by mosquitoes" *Clin Microbiol Rev*, 2000, 13:651-661.

Bueler, H. "Adeno-associated viral vectors for gene transfer and gene therapy" *Biol Chem*, 1999, 380:613-622.
Caplen, N. et al. "Specific inhibition of gene expression by small double-stranded RNAs in invertebrate and vertebrate systems" *Proc. Nal. Acad. Sci. USA*, 2001, 98:9742-9747.
Caplen, N.J. et al. "Inhibition of viral gene expression and replication in mosquito cells by dsRNA-triggered RNA interference" *Mol Ther*, 2002, 6:243-251.
Elbashir, S.M. et al. "Duplexes of 21-nucleotide RNAs mediate RNA interference in cultured mammalian cells" *Nature*, 2001, 411:494-498.
Fire, A. "RNA-triggered gene silencing" *Trends Genet*, 1999, 15:358-363.
Hammond, S.M. et al. "Argonaute2, a link between genetic and biochemical analyses of RNAi" *Science*, 2001, 293:1146-1150.
Ho, L.J. et al. "Infection of human dendritic cells by dengue virus causes cell maturation and cytokine production" *J Immunol*, 2001, 166:1499-1506.
Hutvágner, G. et al. "A cellular function for the RNA-interference enzyme dicer in the maturation of the *let*-7 small temporal RNA" *Science*, 2001, 293:834-838.
Ilves, H. et al. "Retroviral vectors designed for targeted expression of RNA polymerase III-driven transcripts: a comparative study" *Gene*, 1996, 171:203-208.
Kay, M.A. et al. "Viral vectors for gene therapy: the art of turning infectious agents into vehicles of therapeutics" *Nature Med*, 2001, 7:33-40.
Libraty, D.H. et al. "Human dendritic cells are activated by dengue virus infection: enhancement by gamma interferon and implications for disease pathogenesis" *J Virol*, 2001, 75:3501-3508.
Ludewig, B. et al. "Protective antiviral cytotoxic T cell memory is most efficiently maintained by restimulation via dendritic cells" *J Immunol*, 1999, 163:1839-1844.
Marovich, M. et al. "Human dendritic cells as targets of dengue virus infection" *J Investig Dermatol Symp Proc.*, 2001, 6:219-224.
Men, R. et al. "Dengue type 4 virus mutants containing deletions in the 3' noncoding region of the RNA genome: analysis of growth restriction in cell culture and altered viremia pattern and immunogenicity in Rhesus monkeys" *J Virol*. 1996, 70:3930-3937.
Paul, C.P. et al. "Effective expression of small interfering RNA in human cells" *Nature Biotech.*, 2002, 20:505-508.
Ponnazhagan, S. et al. "Adeno-associated virus type 2-mediated transduction of human monocyte-derived dendritic cells: implications for ex vivo immunotherapy" *J Virol*, 2001, 75:9493-9501.
Proutski, V. et al. "Secondary structure of the 3' untranslated region of flaviviruses: similarities and differences" *Nucleic Acids Res*, 1997, 25:1194-1202.
Provost, P. et al. "Ribonuclease activity and RNA binding of recombinant human Dicer" *Embo J*, 2002, 21:5864.
Rauscher, S: et al. "Secondary structure of the 3'-noncoding region of flavivirus genomes: comparative analysis of base pairing probabilities" *RNA*, 1997, 3:779-791.
Roy, K. et al. "Oral gene delivery with chitosan-DNA nanoparticies generates immunologic protection in a murine model of peanut allergy" *Nat Med*, 1999, 5:387-391.
Srivastava, A. "Obstacles to human hematopoletic stem cell transduction by recombinant adeno-associated virus 2 vectors" *J Cell Blochem Suppl*, 2002, 38:39-45.
Stämpfli, M.R. et al. "GM-CSF transgene. expression in the airway allows aerosolized ovalbumin to induce allergic sensitization in mice" *J Clin Invest*, 1998, 102:1704-1714.
Stark, G.R. et al. "How cells respond to interferons" *Annu Rev Biochem*, 1998, 67:227-264.
Tuschl, T. "Expanding small RNA interference" *Nature Blotechnol.*, 2002, 20:446-448.
Vaughn, D.W. et al. "Dengue in the early febrile phase: viremia and antibody responses" *J Infect Dis*, 1997, 176:322-330.
Walter, D.M. et al. "IL-18 gene transfer by adenovirus prevents the development of and reverses established allergen-induced airway hyperreactivity" *J Immunol*, 2001, 166:6392-6398.
Wu, S.J. et al. "Human skin Langerhans cells are targets of dengue virus infection" *Nature Med*, 2000, 6:816-820.

(56) References Cited

OTHER PUBLICATIONS

Zaiss, A-K. et al. "Differential activation of innate immune responses by adenovirus and adeno-associated virus vectors" *J Virol*, 2002, 76:4580-4590.

Behera, A.K. et al. "Adenovirus-Mediated Interferon γ Gene Therapy for Allergic Asthma: Involvement of Interleukin 12 and STAT4 Signaling" *Human Gene Therapy*, Sep. 2002, 13:1697-1709.

Behera, A.K. et al. "2'-5' Oligoadenylate Synthetase Plays a Critical Role in Interferon-γ Inhibition of Respiratory Syncytial Virus Infection of Human Epithelial Cells" *The Journal of Biological Chemistry*, Jul. 2002, 277(28):25601-25608.

Bitko, V. et al. "Phenotypic silencing of cytoplasmic genes using sequence-specific double-stranded short interfering RNA and its application in the reverse genetics of wild type negative-strand RNA viruses" *BMC Microbiology*, 2001, 1(34):1-11.

Bossert, B. et al. "Respiratory Syncytial Virus (RSV) Nonstructural (NS) Proteins as Host Range Determinants: a Chimeric Bovine RSV with NS Genes from Human RSV IS Attenuated in Interferon-Competent Bovine Cells" *Journal of Virology*, May 2002, 76(9):4287-4293.

Bossert, B. et al. "Nonstructural Proteins NS1 and NS2 of Bovine Respiratory Syncytial Virus Block Activation of Interferon Regulatory Factor 3" *Journal of Virology*, Aug. 2003, 77(16):8661-8668.

Dorn, G. et al. "siRNA relieves chronic neuropathic pain" *Nucleic Acids Research*, 2004, 32(5):e49.

Hallak, L.K. etal. "Iduronic Acid-Containing Glycosaminoglycans on Target Cells Are Required for Efficient Respiratory Syncytial Virus Infection" *Virology*, 2000, 271:264-275.

Hellerman, G.R. et al. "Genetic therapy: on the brink of a new future" *Genetic Vaccines and Therapy*, 2003, 1(1):1-2.

Jairath, S. et al. "Inhibition of respiratory syncytial virus replication by antisense oligodeoxyribonucleotides" *Antiviral Research*, 1997, 33:201-213.

Jin, H. etal. "Recombinant Respiratory Syncytial Viruses with Deletions in the NSI, NS2, SH, and M2-2 Genes are Attenuated in Vitro and in Vivo" *Virology*, 2000, 273:210-218.

Kumar, M. et al. "Intranasal IFN-γ gene transfer protects BALB/c mice against respiratory syncytial virus infection" *Vaccine*, 2000; 18:558-567.

Kumar, M. et al. "Intranasal Gene Transfer by Chitosan-DNA Nanospheres Protects BALB/c Mice Against Acute Respiratory Syncytial Virus Infection" *Human Gene Therapy*, Aug. 2002, 13:1415-1425.

Kumar, M. et al. "Chitosan IFN-γ-pDNA Nanoparticle (CIN) Therapy for Allergic Asthma" *Genetic Vaccines and Therapy*, 2003, 1(3):1-10.

Leaman, D.W. et al. "Targeted Therapy of Respiratory Syncytial Virus in African Green Monkeys by Intranasally Administered 2-5A Antisense" *Virology*, 2002, 292:70-77.

Matsuse, H. et al. "Recurrent Respiratory Syncytial Virus Infections in Allergen-Sensitized Mice Lead to Persistent Airway Inflammation and Hyperresponsiveness" *The Journal of Immunology*, 2000, 164:6583-6592.

Mohapatra, S. "Mucosal gene expression vaccine: a novel vaccine strategy for respiratory syncytial virus" *The Pediatric Infectious Disease Journal*, Feb. 2003, 22(2):S100-S104.

Murphy, B.R. "Live-attenuated virus vaccines for respiratory syncytial and parainfluenza viruses: applications of reverse genetics" *The Journal of Clinical Investigation*, Jul. 2002, 110(1):21-27.

Lazar, I. et al. "Human Metapneumovirus and Severity of Respiratory Syncytial Virus Disease" *Emerging Infectious Diseases*, Jul. 2004, 10(7):1318-1320, NCBI accession No. M74568.

Deplanche, M. et al. "In vivo evidence for quasispecies distributions in the bovine respiratory syncytial virus genome" *Journal of General Virology*, 2007, 88:1260-1265, NCBI accession No. NC_001989.

Pan, W. et al. "Isolation of virus-neutralizing RNAs from a large pool of random sequences" *Proc. Natl. Acad. Sci. USA*, Dec. 1995, 92:11509-11513.

Schlender, J. et al. "Bovine Respiratory Syncytial Virus Nonstructural Proteins NS1 and NS2 Cooperatively Antagonize Alpha/Beta Interferon-Induced Antiviral Response" *Journal of Virology*, 2000, Sep. 2000, 74(18):8234-8242.

Soutschek, J. et al. "Therapeutic silencing of an endogenous gene by systemic administration of modified siRNAs" *Nature*, Nov. 2004, 432:173-178.

Spann, K.M. et al. "Suppression of the Induction of Alpha, Beta, and Gamma Interferons by the NS1 and NS2 Proteins of Human Respiratory Syncytial Virus in Human Epithelial Cells and Macrophages" *Journal of Virology*, Apr. 2004, 78(8):4363-4369.

Stein, C.A. "The experimental use of antisense oligonucleotides: a guide for the perplexed" *The Journal of Clinical Investigation*, 2001, 108:641-644.

Teng, M.N. et al. "Altered Growth Characteristics of Recombinant Respiratory Syncytial Viruses Which Do Not Produce NS2 Protein" *Journal of Virology*, Jan. 1999, 73(1):466-473.

Teng, M.N. et al. "Recombinant Respiratory Syncytial Virus That Does Not Express the NS1 or M2-2 Protein Is Highly Attenuated and Immunogenic in Chimpanzees" *Journal of Virology*, Oct. 2000, 74(19):9317-9321.

Zhang, W. et al. "Attenuation of dengue virus infection by adeno-associated virus-mediated siRNA delivery" *Genetic Vaccines and Therapy*, 2004, 2(8):1-10.

Zhang, X. et al. "Small Interfering RNA Targeting Heme Oxygenase-1 Enhances Ischemia-Reperfusion-induced Lung Apoptosis" *The Journal of Biological Chemistry*, Mar. 2004, 279(11):10677-10684.

Zhao, C.A. et al. "Inhibition of respiratory syncytial virus replication in cultured cells by RNA-cleaving DNAzyme" *Chinese Journal of Pediatrics*, 2003, 41(8): 594-597, Medline XP002513933 Database accession No. NLM14744382.

Reich, S.J. et al. "Small interfering Rna (siRNA) targeting *VEGF* effectively inhibits ocular neovascularization in a mouse model" *Molecular Vision*, 2003, 9:210-216.

Subramanya, S. et al. "Targeted Delivery of Small Interfering RNA to Human Dendritic Cells to Suppress Dengue Virus Infection and Associated Proinflammatory Cytokine Production" *Journal of Virology*, Mar. 2010, 84(5):2490-2501.

Chhabra, A. et al. "Silencing of Endogenous IL-10 in Human Dendritic Cells Leads to the Generation of an Improved CTL Response Against Human Melanoma Associated Antigenic Epitope, MART-1" *Clin Immunol.*, Mar. 2008, 126(3):251-259.

Heale, B.S.E. et al. "siRNA target site secondary structure predictions using local stable substructures" *Nucleic Acids Research*, 2005, 33(3):e30, pp. 1-10.

Hill, J.A. et al. "Immune Modulation by Silencing IL-12 Production in Dendritic Cells Using Small Interfering RNA" *The Journal of Immunology*, 2003, 171:691-696.

Kretschmer-Kazemi, R. et al. "The activity of siRNA in mammalian cells is related to structural target accessibility: a comparison with antisense oligonucleotides" *Nucleic Acids Research*, 2003, 31(15):4417-4424.

Li, M. et al. "Immune Modulation and Tolerance Induction by ReIB-Silenced Dendritic Cells through RNA Interference" *The Journal of Immunology*, 2007, 178:5480-5487.

Nair, M.P.N. et al. "RNAi-directed Inhibition of DC-Sign by Dendritic Cells: Prospects for HIV-1 Therapy" *The AAPS Journal*, 2005, 7(3):E572-E578.

Nawtaisong, P. et al. "Effective suppression of Dengue fever virus in mosquito cell cultures using retroviral transduction of hammerhead ribozymes targeting the viral genome" *Virology Journal*, 2009, 6:73, pp. 1-17.

Qian, H. et al. "Silencing CD40 in Dendritic Cells by siRNA" *12th International Congress of Immunology and 4th Annual Conference of FOCIS*, Montreal, Canada, Jul. 18-23, 2004, 2004, pp. 339-348.

Shao, Y. et al. "Effect of target secondary structure on RNAi efficiency" *RNA*, 2007, 13:1631-1640.

Westerhout, E.M, et al. "A systematic analysis of the effect of target RNA structure on RNA interference" *Nucleic Acids Research*, 2007, 35(13):4322-4330.

Yoshinari, K. etal. "Effects on RNAi of the tight structure, sequence and position of the targeted region" *Nucleic Acids Research*, 2004, 32(2):691-699.

(56) References Cited

OTHER PUBLICATIONS

Ambion (Oct. 2002) TechNotes 9(5), "Selecting siRNA Sequences to Incorporate into the pSilencer Vectors" [online, retrieved on Nov. 5, 2008] from internet <URL: http://www.ambion.com>, 2 pages.

Hu, W-Y. et al. "Inhibition of Retroviral Pathogenesis by RNA Interference" *Current Biology*, Aug. 6, 2002, 12:1301-1311.

Jayasena, S.D. "Designer siRNAs to overcome the challenges from the RNAi pathway" *Journal of RNAi and Gene Silencing*, 2006, 2(1):109-117.

Krueger, U. et al. "Insights into Effective RNAi Gained from Large-Scale siRNA Validation Screening" *Oligonucleotides*, 2007, 17:237-250.

Luo, K.Q. et al. "The gene-silencing efficiency of siRNA is strongly dependent on the local structure of mRNA at the targeted region" *Biochemical and Biophysical Research Communications*, 2004, 318:303-310.

Rutz, S. et al. "Towards in vivo application of RNA interference—new toys, old problems" *Arthritis Research & Therapy*, 2004, 6(2):78-85.

Schubert, S. et al. "Local RNA Target Structure Influences siRNA Efficacy: Systematic Analysis of Intentionally Designed Binding Regions" *J Mol Biol*, 2005, 348:883-893.

Schubert, S. et al. "Oligonucleotide-Based Antiviral Strategies" *Handbook Exp Pharmacol*, 2006, 173:261-287.

Paddison, P.J. et al. "Short hairpin RNAs (shRNAs) induce sequence-specific silencing in mammalian cells" *Genes & Development*, 2002, 16:948-958.

Zhang, Y. et al. "In Vivo knockdown of gene expression in brain cancer with intravenous RNAi in adult rats" *J Gene Med. 2003*, 5:1039-1045.

Miyagishi, M. et al. "Comparison of the Suppressive Effects Antisense Oligonucleotides and siRNAs Directed Against the Same Targets in Mammalian Cells," *Antisense and Nucleic Acid Druge Development*, Feb. 2003, 13(1):1-7.

\* cited by examiner pSMWZ- DEN-si-PrM

FIG. 4A pSMWZ-DEN-si-3'UTR

FIG. 4B

METHODS FOR ATTENUATING DENGUE VIRUS INFECTION

CROSS-REFERENCE TO RELATED APPLICATION

The present application is the National Stage of International Application No. PCT/US2004/005566, filed Feb. 23, 2004, which claims benefit of U.S. Provisional Application Ser. No. 60/319,964, filed Feb. 21, 2003, and U.S. Provisional Application Ser. No. 60/320,108, filed Apr. 15, 2003, which are hereby incorporated by reference herein in their entirety, including any figures, tables, nucleic acid sequences, amino acid sequences, or drawings.

BACKGROUND OF THE INVENTION

Regulating gene expression either by increasing expression or decreasing expression is considered beneficial for treatment of human diseases. This is especially important in those diseases in which master regulatory genes have been identified. While a majority of efforts have been extended toward enhancing gene expression, down-regulating specific gene expression is equally important. A naturally occurring gene-silencing mechanism triggered by double-stranded RNA (dsRNA), designated as small interfering RNA (siRNA), has emerged as a very important tool to suppress or knock down gene expression in many systems. RNA interference is triggered by dsRNA that is cleaved by an RNAse-III-like enzyme, Dicer, into 21-25 nucleotide fragments with characteristic 5' and 3' termini (Provost, P. D. et al. *Embo J,* 2002, 21:5864). These siRNAs act as guides for a multi-protein complex, including a PAZ/PIWI domain containing the protein Argonaute2, that cleaves the target mRNA (Hammond, S. M. et al. *Science,* 2001, 293:1146-1150). These gene-silencing mechanisms are highly specific and potent and can potentially induce inhibition of gene expression throughout an organism.

The last decade has seen tremendous progress in gene expression technology, including the continued development of both non-viral and viral vectors. The non-viral approach to gene expression involves the use of plasmid DNAs (pDNAs) which have a number of advantages, including ease of use and preparation, stability and heat resistance, and unlimited size. The plasmids do not replicate in mammalian hosts and do not integrate into host genomes, yet they can persist in host cells and express the cloned gene for a period of weeks to months.

Furthermore, several investigators have utilized a replication-deficient episomal adenovirus as a vehicle for transient gene expression. Adenoviral vectors are very efficient at transducing target cells in vitro and in vivo and permit transgene expression in a dose-dependent manner (Stampfli, M. R. et al., *J Clin Invest,* 1998, 102:1704-1714; Walter, D. M. et al., *J Immunol,* 2001, 166:6392-6398). However, adenoviral vectors can cause acute inflammation and an immune response to viral vector-encoded antigens. While efforts to improve viral vectors continue, acute inflammation and immunogenicity to viruses remain the major stumbling blocks to the application of viral-mediated gene transfer. The adeno-associated virus has been considered particularly advantageous because it is non-pathogenic in humans and it causes less inflammation and immunogenicity than adenovirus.

In order to utilize siRNA technology in mammalian cells, gene transfer methods must be employed. However, a majority of common chronic diseases and viral infections are multifactoral and it is difficult to effectively treat a disease by only silencing one particular gene. It would not only be advantageous to create vectors that employ siRNA technology to target one specific gene responsible for a disease, but to create a single vector capable of targeting and down-regulating several genes responsible for multifactoral diseases. Alternatively, in some multifactoral diseases, it would be advantageous to simultaneously express certain endogenous genes, such as endogenous tumor suppressor genes, or exogenous genes, such as exogenous apoptotic genes.

Infection by Dengue Virus (DV, also referred to herein as DEN) is one type of viral infection where siRNA technology would be advantageous. The need for safe and effective inhibition of DV infection (e.g., prophylaxis or treatment), a category A mosquito-borne human pathogen, is a critical global priority. DV causes dengue hemorrhagic fever/dengue shock syndrome (DBF/DSS), which is associated with heterologous secondary DV infection and affects thousands of people worldwide. Moreover, the incidence of DHF/DSS is increasing in the Western Hemisphere. Currently, there are no specific antiviral treatments available. Although many different approaches are being taken to develop prophylactic DEN vaccines, none have been licensed for public health use.

DV belongs to the family of Flaviviruses and is an enveloped single plus-stranded RNA virus with four distinct serotypes. The DEN genome of approximately 11,000 nucleotides encodes a polyprotein (C-prM-E-NS1-NS2a-NS3-NS4a-NS4b-NS5) consisting of three structural proteins (C, prM and E) and seven nonstructural proteins. The open reading frame is flanked by a 100 nucleotide-long noncoding region (NCR) at the 5' end and a 400 to 600 nucleotide-long NCR at the 3'end (Lindenbach, B. & Rich, C. M. Fields Virology, Lippincott Williams & Wilkins. 2000). Although the mechanism of DV pathogenesis is not completely clear, DV typically appears to replicate locally in skin or blood dendritic cells (DCs) and secondary infection and by antibody-dependent enhancement (ADE) may also involve DCs, monocytes, and macrophages. An in vivo gene-silencing approach using siRNA to decrease DV replication is an effective antiviral approach aimed at attenuating the DV viral burden and potentially protecting infected subjects from DHF/DSS.

The mechanism of siRNA is a well-characterized phenomenon that has proven effective in silencing a number of genes of different viruses including those of DV (Fire, A. *Trends Genet,* 1999, 15:358; Blair, C. D. et al. *Clin Microbiol Rev,* 2000, 13:651; Adelman, Z. N. et al. *Insect Mol Biol,* 2001, 10:265; Caplen, N. J. et al. *Mol Ther,* 2002, 6:243). The plus-sense RNA genome of DV must first be translated into the viral polyprotein for infection to occur, and this makes it an excellent target for siRNA. Plasmids encoding antisense DV RNA could be introduced into cells prior to infection, and when dengue virions enter and their RNA is uncoated, the complementary interfering RNAs bind to it and cause cleavage by a host RNase. Adelman et al. (Adelman, Z. N. et al. *Insect Mol. Biol.,* 2001, 10:265-273) transfected mosquito cells with a plasmid encoding a DV-2 inverted RNA repeat, and subsequently challenged them with DV-2. Production of viral envelope protein and genomic RNA was greatly reduced in those cells expressing the RNA construct. Small (~20 nt) RNAs were identified in the cells consistent with the activation of the RNA-interference system. Although the method has only been used to block DV replication in insect cells, siRNA is a workable strategy for in vivo protection from DV and other viral infections. siRNA oligonucleotides directed against the target region near the translation initiation site of DV virus RNA were the most effective at blocking replication (Caplen, N. J. et al. *Mol Ther*, 2002, 6:243).

BRIEF SUMMARY OF THE INVENTION

The present invention includes a vector for modulating multiple genes, wherein the vector comprising a plurality of expression cassettes, including: (a) at least one gene promoting cassette containing a first polynucleotide operably-linked to a first promoter sequence; and (b) at least one gene suppressing cassette containing a second polynucleotide operably-linked to a second promoter sequence, wherein the second polynucleotide encodes a short interfering RNA (siRNA) molecule that reduces expression of a target gene by RNA interference. Preferably, the polynucleotide of the gene promoting cassettes of the vector of the invention encodes a desired polypeptide, such as an enzyme, cytokine, growth factor, or hormone.

The promoter sequences of the gene promoting cassettes and the gene suppressing cassettes can each be constitutive, such as cytomegalovirus (CMV), or tissue-specific. The promoter sequences of the gene promoting cassettes and the gene suppressing cassettes can each be inducible or non-inducible.

In another aspect, the present invention includes a method of modulating the expression of multiple genes within a host by administering a vector of the present invention to the host, wherein the first polynucleotide sequence is expressed in the host, wherein the second polynucleotide is transcribed to produce the siRNA molecule, and wherein the siRNA molecule is capable of reducing expression of a target gene by RNA interference.

The present invention also includes a vector for inhibiting the expression of viral or bacterial genes in a host, wherein the vector comprises at least one gene suppressing cassette containing a polynucleotide operably-linked to a promoter sequence, wherein the polynucleotide encodes an siRNA molecule that reduces expression of a target viral or bacterial gene within the host by RNA interference. Any viral or bacterial gene may be targeted for interference. In one embodiment, the viral gene is a Dengue virus (DV) gene. Any gene of the Dengue virus genome (approximately 11,000 nucleotides) can be targeted. The target gene can encode a structural protein or non-structural protein, for example. Typically, the target Dengue gene will encode at least one protein selected from the group consisting of C, prM, E, NS1, NS2a, NS3, NS4a, NS4b, and NS5. Optionally, the vector further includes at least one gene promoting cassette comprising a polynucleotide operably-linked to a promoter sequence. In another aspect, the present invention includes a method of inhibiting the expression of bacterial or viral genes (such as Dengue virus genes) within a host by administering the vector to the host, wherein the polynucleotide sequence is transcribed to produce the siRNA molecule, and wherein the siRNA molecule is capable of reducing expression of a target bacterial or viral gene (such as Dengue virus) within the host by RNA interference. Thus, the present invention includes methods of inhibiting bacterial or viral infections (such as Dengue virus) by administering such vectors to the host.

In further aspect, the present invention includes pharmaceutical compositions comprising an effective amount of any the vectors of the present invention and a pharmaceutically acceptable carrier.

In another aspect, the present invention includes methods for producing the vectors of the present invention.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

For a fuller understanding of the nature and objects of the invention, reference should be made to the following detailed description, taken in connection with the accompanying drawings, in which:

FIGS. 3A-3C show micrographs of untransfected HEK-293 cells (FIG. 3A), HEK-293 cells transfected with pVAX-EGFP (FIG. 3B), and HEK-293 cells transfected with pVAX-EGFP and pSMWZ-1-siEGFP (FIG. 3C). FIG. 3D is a bar graph showing the percent EGFP-positive cells following: i) no transfection, ii) transfection with pVAX-EGFP, iii) transfection with pVAX-EGFP and pSMWZ-1-RSV-siNS1, and iv) transfection with pVAX-EGFP and pSMWZ-1-siEGFP.

FIGS. 4A and 4B show that Si-DEN expression decreases Dengue virus type 2 (DEN-2) infection in cultured VERO cells. Two siRNA oligos targeting the PRM gene of DEN-2 were cloned separately into pSMWZ-1. RSV-siNS1 oligo (as control) was cloned into pSMWZ-1. To test the function of pSMWZ-DEN-siPRM and pSMWZ-DEN-si3'UTR, 1×10⁵ VERO cells were seeded into six-well tissue culture plates and incubated at 37°/5% CO₂ until the cells reached 50% confluency. Cells were then transfected with either pSMWZ-DEN-siPRM, pSMWZ-DEN-si3'UTR, or pSMWZ-1-RSV-siNS1 (kSv) using 0, 10 or 25 mg of plasmid in lipofectin reagent. After 48 hours of transfection, cells were incubated with DEN-2 virus. The cells were then infected with DEN-2 virus (at multiplicity of infection of 0.1). Those cells infected with DEN-2 virus were identified by flow cytometry using an antibody to DEN-2 virus (MICROBIX BIOSYSTEMS INC, Clone No 3H5). FIG. 4A is a bar graph showing the percent DEN-2-infected cells after: i) transfection with pSMWZ-1-RSV-siNS1 (RSV) followed by incubation with DEN-2 virus and ii) transfection of pSMWZ-DEN-siPrM (DEN) followed by incubation with DEN-2 virus. FIG. 4B is a bar graph showing the percent DEN-2-infected cells after: i) transfection of pSMWZ-1-RSV-siNS1 (RSV) followed by incubation with DEN-2 virus and ii) transfection of pSMWZ-DEN-si3'UTR (DEN) followed by incubation with DEN-2 virus.

FIGS. 5A and 5B show that pSMWZ-siDEN suppresses DEN-2 virus replication and AAVsiEGFP inhibits the expression of EGFP in cultured cells. Vero cells were transfected with pSMWZ-siDEN3UT or pSMWZ-siDENpreM plasmid. Two days later, the cells were infected with DEN-2 virus (MOI of 0.1) and 5 days later, the numbers of DEN-2 virus infected cells were counted by fluorescence microscopy, as shown in FIG. 5A. Data are means±SEM. *$p<0.05$ when compared with control group DEV-2. HEK293 cells were infected with different concentrations of AAVsiEGFP, and three days later the cells were transfected with pEGFP. EGFP-positive cells were counted by fluorescence microscopy, as shown in FIG. 5B. Statistically significant differences, **$p<0.01$, when compared to pEGFP plasmid control, AAV-siRSV ($10^7$) and AAVsiEGFP ($10^8$) group, respectively.

FIGS. 6A-6F show that AAVsiDEN expression decreases DEN-2 virus infection in cultured Vero cells. Cells were infected with different amounts (PFU/ml) of AAV carrying the siDEN3UT silencing cassette and, after 2 days, the cells were infected with DEN-2 virus (MOI of 0.1). Five days later, the numbers of DEN-2 virus infected cells were quantified by flow cytometry.

FIGS. 7A-7D show suppression of DEN-2 replication in dendritic cells (DCs) by siDEN. DCs were isolated from human peripheral blood and cultured in DMEM medium supplemented with FBS, IL-4 and GM-CSF. Floating DCs were harvested on day 7, infected with AAVsiDEN, and two days later the cells were reinfected with DEN-2 at 0.1 MOI. DCs were harvested 5 days after DEN-2 infection and DEN-2 titers were measured by flow cytometry.

FIG. 8 shows that AAV-mediated siDEN3UT expression significantly decreased DEN-2 virus titer compared to control. Supernatants from DEN-infected DCs were taken and inoculated into culture plates containing confluent Vero cell monolayers. After virus adsorption, the Vero cells were overlaid with agarose and stained with 1% neutral red. Viral plaques were counted at 48 h after neutral red overlay. Data are the averages of two independent experiments. *$p<0.05$ when compared with control group DEV-2 in PFU value.

FIG. 9 shows that AAVsiDEN reduces apoptosis in human DCs infected with DEN-2. DCs were isolated from human peripheral blood and infected with AAVsiDEN following by DEN-2. Five days after infection, infected DCs were put onto slides and apoptosis was determined using the terminal dUTP nick end-labeling assay. Nuclei were stained with diamidinophenylindole (DAPI). Representative fields visualized by fluorescence microscopy are shown.

FIG. 10 shows differential expression of cytokines in the supernatants of infected DCs. Supernatants from DEN-2-infected DCs with or without siDEN treatment were harvested at the indicated time points and analyzed by CBA and ELISA to measure the concentrations of cytokines. Data are the averages of two independent experiments. *$p<0.01$ in comparison with the value of DCs within individual group.

BRIEF DESCRIPTION OF THE SEQUENCES

SEQ ID NO: 1 is the oligonucleotide sequence encoding the siRNA targeting the EGFP gene (si-GFP):

```
5'-GGC GAT GCC ACC TAC GGC AAG CTT CTC GAT TCG AAG
CTT GCC GTA GGT GGC ATC GCC CTT TTT G-3'
```

SEQ ID NO: 2 is the oligonucleotide sequence encoding the siRNA targeting the nonstructural protein 1(NS1) gene (GenBank Accession No. M11486) of human respiratory syncytial virus (RSV) (RSV si-NS1):

```
5'-GGC AGC AAT TCA TTG AGT ATG CTT CTC GAA ATA AGC
ATA CTC AAT GAA TTG CTG CCT TTT TG-3'.
```

SEQ ID NO: 3 is the oligonucleotide sequence encoding the siRNA targeting the pre-membrane protein (prM) gene (GenBank Accession No. M29095) of Dengue virus type 2 (DEN-si-PrM):

```
5'-GGA AGA CAT AGA TTG TTG GTG CAC TCG AGT CAA CGT
GCA CCA ACA ATC TAT GTC T TC CCT TTT TG-3'.
```

SEQ ID NO: 4 is the oligonucleotide sequence encoding the siRNA targeting the 3' UTR (GenBank Accession No. M29095) of Dengue virus type 2 (DEN-si-3'UTR):

```
5'-GGA AAA ACA GCA TAT TGA CGC TGC TCG AGT CAA CGC
AGC GTC AAT ATG CTG TTT TTC CCT TTT TG-3'.
```

DETAILED DISCLOSURE OF THE INVENTION

The present invention includes a vector for modulating multiple genes, wherein the vector comprising a plurality of expression cassettes, including: (a) at least one gene promoting cassette containing a first polynucleotide operably-linked to a first promoter sequence; and (b) at least one gene suppressing cassette containing a second polynucleotide operably-linked to a second promoter sequence, wherein the second polynucleotide encodes a short interfering RNA (siRNA) molecule that reduces expression of a target gene by RNA interference. The siRNA molecule is preferably an RNA duplex comprising a sense region and an antisense region, wherein the antisense region includes a plurality of contiguous nucleotides that are complementary to a messenger RNA sequence encoded by the target gene. In one embodiment, the polynucleotide encoding the siRNA comprises at least one nucleotide sequence selected from the group consisting of SEQ ID NO:1, SEQ ID NO:2, SEQ ID NO:3, and SEQ ID NO:4.

The present invention also includes a vector for inhibiting the expression of viral or bacterial genes in a host, wherein the vector comprises at least one gene suppressing cassette containing a polynucleotide operably-linked to a promoter sequence, wherein the polynucleotide encodes an siRNA molecule that reduces expression of a target viral or bacterial gene within the host by RNA interference. Any bacterial or viral gene may be targeted for interference, such as RSV genes and/or DV genes. In one embodiment, the viral gene is a DV gene. Typically, the target Dengue gene(s) will encode at least one protein selected from the group consisting of C, prM, E, NS1, NS2a, NS3, NS4a, NS4b, and NS5. Preferably, the nucleotide sequence(s) targeted by the siRNA is common to 2, 3, or all 4 serotypes of DV. In one embodiment, the polynucleotide encoding the siRNA comprises the nucleotide sequence of SEQ ID NO:3 or SEQ ID NO:4. Preferably, viral genes that are normally expressed in an earlier stage of the viral multiplication cycle are targeted for inhibition. Optionally, the vector further includes at least one gene promoting cassette a polynucleotide operably-linked to a promoter sequence.

Figure 1A:
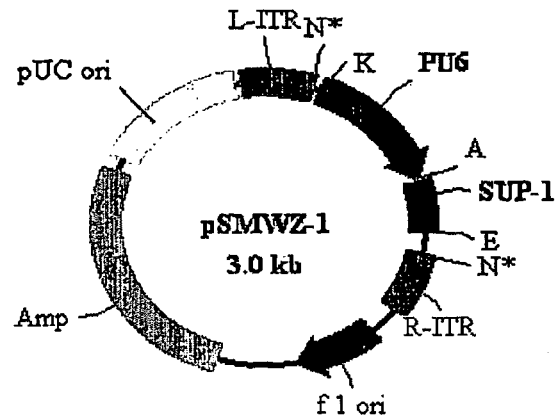
FIGS. 1A-1E show vector maps of pSMWZ-1, pSMWZ-2, and pSMWZ-3, which are capable of expressing 1, 2 or 3 suppressor cassette(s) (FIGS. 1A-1C), a schematic diagram of a vector preparation scheme (FIG. 1D), and a schematic diagram of a suppressor cassette (FIG. 1E). Plasmid vector pSMWZ-1 was created by the following steps: (i) the pCMV-MCS plasmid (STRATAGENE) was digested with Not I and the larger fragment, containing the ampicillin resistance gene, was ligated to the synthetic adapter, containing, in order, Not I-Kpn I-Apa I-Xho I-Hind III-EcoR I-Bam HI-Sac II-Sac I-Cla I-Sal I-Bgl II-Not I; (ii) the suppressor cassette, containing the mouse U6 promoter linked to a multiple cloning site, was obtained by PCR amplification, using specific primers with the desired restriction sites from the template pSilencer 1.0-U6 (AMBION), and inserted in the adaptor at the appropriate sites; and (iii) the modified. pCMV-MCS plasmid was digested with Not I and the smaller fragment was ligated to the 2.9 kb fragment of pAAV-MCS (STRATAGENE) obtained following its Not I digestion. Plasmids pSMWZ-2 and pSMWZ-3 can be created by inserting additional suppressor cassettes (i.e., additional gene suppressing cassettes) at the Not I site. Abbreviations: PU6, U6 promoter; SUP, Suppressor; N, Not I; K, Kpn I; A, Apa I; E, Eco R I; B, Bam H I; S, SacI; C, Cla I and B, Bgl II.

The siRNA molecule encoded by each gene suppressing cassette is preferably in the range of about 45 to about 60 nucleotides in length; however, the size of the siRNA molecule can be larger or smaller, depending upon the size of the target polynucleotide sequence within the target gene. The size of each gene suppressing cassette (including the siRNA-encoding polynucleotide and promoter sequence) will depend upon the size of the desired target mRNA and promoter sequence utilized. For example, each gene suppressing cassette (including the siRNA-encoding polynucleotide and promoter sequence) can be about 410 nucleotides in length. Preferably, the antisense region is in the range of about 13 to about 27 nucleotides in length. More preferably, the antisense region is in the range of about 19 to about 21 nucleotides in length. The siRNA produced by the vectors of the present invention can be designed in accordance with Elbashir et al. (*Nature*, 2001, 494-498), Caplen et al. (*Proc. Natl. Acad. Sci. USA*, 2001, 98:9742-9747), and Hutvagner et al. (*Science* 293:834-838); which are hereby incorporated by reference herein in their entirety). This design involves the siRNA having a dinucleotide 3' overhang, which has been demonstrated to bypass the antiviral response and induce gene specific silencing in mammalian cells.

The sense region and the antisense region of the siRNA molecule are connected. Preferably, the sense region and antisense region are covalently connected via a linker molecule (also referred to herein as a "space"), such as a polynucleotide linker. The polynucleotide linker can be various lengths. Preferably, the linker is in the range of about 6 to 12 nucleotides in length.

In a preferred embodiment, the siRNA molecule is partially self-complementary and, therefore, forms a stem and loop structure. The sense region and antisense region of the RNA duplex contain one or more mismatches such that a bulge or secondary structure (such as a hairpin structure) is formed. Preferably, the RNA duplex contains within the range of about 4 to about 23 nucleotide base pair mismatches. More preferably, the RNA duplex contains within the range of about 7 to about 9 nucleotide base pair mismatches. In an alternative embodiment, the siRNA molecule comprises two separate strands (a sense strand and antisense strand) that are substantially complementary so that they form a duplex upon provision of appropriate conditions.

The vectors of the present invention can include a plurality of gene promoting cassettes, wherein each gene promoting cassette contains a polynucleotide encoding the same or a different gene product. Likewise, the vectors of the present invention can include a plurality of gene suppressing cassettes, wherein each gene suppressing cassette contains a polynucleotide encoding an siRNA molecule that targets the same mRNA sequence or different mRNA sequences. For example, each gene suppressing cassette can encode an siRNA molecule that targets an mRNA sequence of two or more different genes. Furthermore, each vector of present invention can include a plurality of gene promoting cassettes and a plurality of gene suppressing cassettes.

Examples of suitable promoters for gene suppressing cassettes include, but are not limited to, U6 promoter, pol II promoter, H1 promoter, and CMV promoter. Optionally, each of the promoter sequences of the gene promoting cassettes and the gene suppressing cassettes can be inducible and/or tissue-specific.

The vectors of the present invention can be non-viral, such as plasmids, or viral vectors, such as adenovirus, adeno-associated virus, poliovirus, lentivirus, HSV, or murine Maloney-based virus.

Preferably, the polynucleotide of the gene promoting cassettes of the vectors of the present invention encode a desired polypeptide, such as an enzyme, cytokine, growth factor, or hormone. For anti-cancer applications, the polynucleotide of the gene promoting cassette can be the coding sequence of a tumor suppressor gene, for example, which is either native or not naturally found and/or not expressed in the host.

In another aspect, the present invention includes a method of modulating the expression of multiple genes within a host by administering an effective amount of a vector of the present invention to the host, wherein the first polynucleotide sequence is expressed in the host, wherein the second polynucleotide is transcribed to produce the siRNA molecule, and wherein the siRNA molecule is capable of reducing expression of a target gene by RNA interference. Preferably, the siRNA molecule is an RNA duplex including a sense region and an antisense region, wherein the antisense region comprises a plurality of contiguous nucleotides that are complementary to a messenger RNA sequence encoded by (and transcribed from) the target gene, and wherein the plurality of contiguous nucleotides hybridize to the messenger RNA sequence, thereby reducing expression of the target gene within the host.

In another aspect, the present invention includes a method of inhibiting the expression of bacterial or viral genes (such as Dengue virus genes) within a host by administering an effective amount of a vector of the invention to the host, wherein the vector comprises at least one gene suppressing cassette containing a polynucleotide operably-linked to a promoter sequence, wherein the polynucleotide encodes an siRNA molecule that reduces expression of a target bacterial or viral gene within the host by RNA interference, wherein the polynucleotide sequence is transcribed to produce the siRNA molecule, and wherein the siRNA molecule is capable of reducing expression of a target bacterial or viral gene (such as Dengue virus) within the host by RNA interference. Accordingly, by inhibiting the expression of bacterial or viral genes, infections caused by such microorganisms can be inhibited (e.g., lessened, alleviated, and/or prevented).

The target gene (the gene targeted by the siRNA molecules of any of the vectors of the present invention) may exist as an endogenous gene that occurs naturally within a host, or an exogenous gene, which does not naturally occur within a host. Exogenous genes may, for example, be a transgene or synthetic gene, a viral or bacterial gene, a gene of a pathogen, parasite, or commensal organism, etc. Preferably, the target gene exists within a vertebrate cell, although the invention is not limited to vectors having polynucleotides encoding siRNA for use in vertebrate cells.

The target gene may include sequences encoding polypeptides or polynucleotide sequences that regulate the replication, transcription, translation or other process important to the expression of the gene. The target gene need not necessarily encode a polypeptide but may encode other cellular components, such as ribosomal RNA, splicosome RNA, transfer RNA, etc. For example, regulatory sequences of Dengue virus can be targeted.

The target sequence may be the entire sequence of the target gene, or, preferably, only a portion of the target gene. Preferably, the target sequence is a contiguous subsequence of the target gene and is from 15 to 30 nucleotides in length. The target sequence may be 15, 16, 17, 18, 19, 20, 21, 22, 23, 24, 25, 26, 27, 28, 29 or 30 nucleotides in length, for example. The size and sequence of the target gene used as the target sequence may be selected by those of skill in the art so as to optimize the interfering effects of the siRNAs produced from the vectors of the invention.

Vectors and methods of the invention therefore provide a means for suppressing the expression of at least one polynucleotide and, optionally, promoting the expression of at least one polynucleotide, within the same vector. The vectors and methods of the invention provides the opportunity to efficiently modulate expression of multiple genes in a wide variety of applications, such as research, industrial, and medical processes. The present invention is particular useful in medical applications where treatment of pathological conditions having multifactoral etiologies is desired. Such conditions often involve the under-expression and over-express of several genes within a patient.

Medical applications include, by way of example, antiviral compositions and therapies, anti-tumor compositions and therapies, and compositions and therapies for inherited disorders. One example of the latter application would be use of vectors of the present invention in therapies to treat autosomal dominant genetic disease such as Huntington's chorea. Additional examples of therapeutic uses include the management of transplant rejection through the treatment of tissues to be introduced into a subject with the vectors of the invention in order to promote the expression of genes promoting transplant acceptance, and to attenuate the expression of genes promoting transplant rejection. For example, hepatocytes may be incubated with vectors of the invention having gene suppressing cassettes encoding siRNA designed to attenuate expression of genes that prompt a host immune response. Another exemplified use involves administering a vector of the invention, wherein one or more gene suppressing cassettes target and suppress a mutant or otherwise dysfunctional gene in the host, and wherein one or more gene promoting cassettes includes a polynucleotide encoding the correct wild-type gene and/or another desired gene to be expressed.

According to the methods of the present invention, the vectors are administered and dosed in accordance with good medical practice, taking into account the clinical condition of the individual patient, the site and method of administration, scheduling of administration, patient age, sex, body weight, and other factors known to medical practitioners. The therapeutically or pharmaceutically "effective amount" for purposes herein is thus determined by such considerations as are known in the art. A therapeutically or pharmaceutically effective amount of nucleic acid molecule is that amount necessary to provide an effective amount of the polynucleotide, or an effective amount of the corresponding transcription product (e.g., siRNA), or the corresponding polypeptide(s) if expressed in vivo. An effective amount of a vector of the present invention, or compositions comprising such vectors, can be an amount sufficient to prevent, treat, reduce and/or ameliorate the symptoms and/or underlying causes of any pathologic condition, such as a disease or other disorder. In some instances, an "effective amount" is sufficient to eliminate the symptoms of the pathologic condition and, perhaps, overcome the condition itself. In the context of the present invention, the terms "treat" and "therapy" and the like refer to alleviating, slowing the progression, prophylaxis, attenuating, or curing of an existing condition. The term "prevent", as used herein, refers to putting off, delaying, slowing, inhibiting, or otherwise stopping, reducing, or ameliorating the onset of such conditions.

Mammalian species which benefit from the disclosed vectors, compositions, and methods include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales.

As used herein, the term "patient", "subject", and "host" are used herein interchangeably and intended to include such human and non-human mammalian species and cells of those species. For example, the term "host" includes one or more host cells, which may be prokaryotic (such as bacterial cells) or eukaryotic cells (such as human or non-human mammalian cells), and may be in an in vivo or in vitro state. Thus, the term "host" is inclusive of whole organisms and their cells. In those cases wherein the polynucleotide utilized comprises a naturally occurring nucleic acid sequence, the polynucleotide can be administered to subjects of the same species or different species from which the nucleic acid sequence naturally exists, for example.

The vectors of the present invention (and compositions containing them) can be administered to a subject by any route that results in delivery of the genetic material (e.g., polynucleotides) and transcription of the polynucleotides of the gene suppressor cassettes into siRNA molecules. For example, the vectors of the present invention can be administered to a host intravenously (I.V.), intramuscularly (I.M.), subcutaneously (S.C.), intradermally (I.D.), orally, intranasally, etc.

Examples of intranasal administration can be by means of a spray, drops, powder or gel and also described in U.S. Pat. No. 6,489,306, which is incorporated herein by reference in its entirety. One embodiment of the present invention is the administration of the vectors as a nasal spray. Alternate embodiments include administration through any oral or mucosal routes such as oral, sublingual, intravaginal or intraanal administration, and even eye drops. However, other means of drug administrations such as subcutaneous, intravenous, and transdermal are well within the scope of the present invention.

The siRNA produced by the vectors of the present invention allows for the modulation, and especially the attenuation, of target gene expression when such a gene is present and liable to expression within a host's cell. Modulation of expression can be partial or complete inhibition of gene function, and can include the up-regulation of other, secondary target genes or the enhancement of expression of such genes in response to the inhibition of the primary target gene.

Attenuation of gene expression may include the partial or complete suppression or inhibition of gene function, transcript processing, or translation of the transcript. In the context of RNA interference, modulation of gene expression is thought to proceed through a complex of proteins and RNA, specifically including small, dsRNA that may act as a "guide" RNA. The siRNA therefore is thought to be effective when its nucleotide sequence sufficiently corresponds to at least part of the nucleotide sequence of the target gene. Although the present invention is not limited by this mechanistic hypothesis, it is highly preferred that the sequence of nucleotides in the siRNA be substantially identical to at least a portion of the target gene sequence.

A target gene generally means a polynucleotide comprising a region that encodes a polypeptide, or a polynucleotide region that regulates replication, transcription or translation or other processes important to expression of the polypeptide, or a polynucleotide comprising both a region that encodes a polypeptide and a region operably linked thereto that regulates expression. The targeted gene can be chromosomal (genomic) or extrachromosomal. It may be endogenous to the cell, or it may be a foreign gene (a transgene). The foreign gene can be integrated into the host genome, or it may be present on an extrachromosomal genetic construct such as a plasmid or a cosmid. The targeted gene can also be derived from a pathogen, such as a virus, bacterium, fungus or protozoan, which is capable of infecting a host organism or cell. Target genes may be viral and pro-viral genes that do not elicit the interferon response, such as retroviral genes. The target gene may be a protein-coding gene or a non-protein coding gene, such as a gene that encodes ribosomal RNAs, splicosomal RNA, tRNAs, etc.

Any gene being expressed in a cell can be targeted using the vectors of the present invention. Preferably, a target gene is one involved in or associated with the progression of cellular activities important to a pathological condition (such as a disease) or is of particular interest as a research object. The following are non-limiting examples of classes of possible target genes that may be used in the methods of the present invention to modulate or attenuate target gene expression: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g., ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g., APC, BRCA1, BRCA2, MADH4, MCC, NF1, NF2, RB1, TP53 and WT1), and enzymes (e.g., ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, pectinesterases, peroxidases, phosphatases, phospholipases, phophorylases, polygalacturonases, proteinases and peptideases, pullanases, recombinases, reverse transcriptases, topoisomerases, xylanases). These are only examples of genes that can be up-regulated (e.g., delivered and expressed via one or more gene promoting cassettes) or down-regulated (e.g., targeted by one or more gene suppressing cassettes) within a host using the vectors of the present invention.

The nucleotide sequence of the siRNA molecule transcribed from the gene suppressor cassette contained within the vectors of the invention is defined by the nucleotide sequence of its target gene. The siRNA molecule comprises a nucleotide sequence that is essentially identical to at least a portion of the target gene. Preferably, the siRNA molecule comprises a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

An siRNA molecule (also referred to herein as an "siRNA") comprises at least a partially duplex structure, the sequence of which is "substantially identical" to at least a portion of the target gene. "Identity", as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated (See, for example: Computational Molecular Biology, Lesk, A. M., ed. Oxford University Press, New York, 1988; Biocomputing: Informatics and Genome Projects, Smith, D. W., ed., Academic Press, New York, 1993; and the methods disclosed in WO 99/32619, WO 01/68836, WO 00/44914, and WO 01/36646, specifically incorporated herein by reference). While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux, J. et al. *Nucleic Acid Res.*, 1984, 12(1):387), BLASTP, BLASTN, and FASTA (Atschul, S. F. et al. *J. Molec. Biol.*, 1990, 215:403) and CLUSTAL (Higgins, D. G. et al. *Comp. Appl. Biosci.* (*CABIOS*), 1992, 8(2):189-191; Thompson, J. D. et al. *Nucleic Acids Res.*, 1994, 22:4673-4680).

The term "polynucleotide", as used herein, refers to a polymeric form of nucleotides of any length, either ribonucleotides or deoxyribonucleotides. This term refers only to the primary structure of the molecule. The term includes double-stranded and single-stranded DNA, as well as double-stranded and single-stranded RNA. Thus, the term includes DNA, RNA, or DNA-DNA, DNA-RNA, or RNA-RNA hybrids, or protein nucleic acids (PNAs) formed by conjugating bases to an amino acid backgone. It also includes modifications, such as by methylation and/or by capping, and unmodified forms of the polynucleotide. The nucleotides may be synthetic, or naturally derived, and may contain genes, portions of genes, or other useful polynucleotides.

In one embodiment, the polynucleotide(s) of the gene promoting cassette comprise DNA containing all or part of the coding sequence for a polypeptide, or a complementary sequence thereof, such as a cytokine or tumor suppressor. An encoded polypeptide may be intracellular, i.e., retained in the cytoplasm, nucleus, or in an organelle, or may be secreted by the cell. For secretion, the natural signal sequence present in a polypeptide may be retained. When the polypeptide or peptide is a fragment of a protein, a signal sequence may be provided so that, upon secretion and processing at the processing site, the desired protein will have the natural sequence. Specific examples of coding sequences of interest for use in accordance with the present invention include the polypeptide-coding sequences disclosed herein. The polynucleotides may also contain, optionally, one or more expressible marker genes for expression as an indication of successful transfection and expression of the nucleic acid sequences contained therein.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

The vectors of the invention are useful for the delivery of polynucleotides to hosts and the inhibition of target gene expression in vitro or in vivo. The term "vector" is used herein to refer to any molecule (e.g., nucleic acid or plasmid) usable to transfer a polynucleotide, such as coding sequence information (e.g., nucleic acid sequence encoding a protein or other polypeptide), to a host. The term "vector" is inclusive of viral vectors and non-viral vectors. A vector typically includes a replicon in which another polynucleotide segment is attached, such as to bring about the replication and/or expression of the attached segment. The term includes expression vectors, cloning vectors, and the like. Thus, the term includes gene expression vectors capable of delivery/transfer of exogenous nucleic acid sequences into a host. The term "expression vector" refers to a vector that is suitable for use in a host (e.g., a subject's cell, tissue culture cell, cells of a cell line, etc.) and contains nucleic acid sequences which direct and/or control the expression of exogenous nucleic acid sequences. Expression includes, but is not limited to, processes such as transcription, translation, and RNA splicing, if introns are present. Nucleic acid sequences can be modified according to methods known in the art to provide optimal codon usage for expression in a particular expression system. The vectors of the present invention may include elements to control targeting, expression and transcription of the nucleic acid sequence in a cell selective manner as is known in the art. The vectors can include a control sequence, such as a promoter for controlling transcription of the exogenous material and can be either a constitutive or inducible promoter to allow selective transcription. The expression vector can also include a selection gene.

The vectors of the present invention can include one or more cloning sites. A "cloning site" refers to a nucleic acid sequence recognized and cleaved by a restriction enzyme. Such cloning sites are useful for the insertion of foreign nucleic acid sequences between two existing nucleic acid sequences which are joined by a cloning site. Some suitable cloning sites useful in the present invention will include, but are not limited to those recognized and cleaved by the restriction enzymes EcoRI, NotI, XbaI, HindIII, BamHI, and KpnI.

A "coding sequence" is a polynucleotide sequence that is transcribed into mRNA and/or translated into a polypeptide. The gene promoting cassette(s) of the vectors of the present invention can each include one or more coding sequences for the same or different polypeptides. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. For example, the vectors of the present invention may be used to deliver coding sequences for proteins or variants or analogs thereof. Techniques for modifying nucleotide sequences, such as site-directed mutagenesis, are well known to those skilled in the art (See, e.g., Sambrook et al., Molecular Cloning: A Laboratory Manual, Second Edition, 1989; DNA Cloning, Vols. I and II, D. N. Glover ed., 1985). Optionally, the polynucleotides used in the vectors of the present invention, and compositions and methods of the invention that utilize such vectors, can include non-coding sequences.

The term "operably-linked" is used herein to refer to an arrangement of flanking control sequences wherein the flanking sequences so described are configured or assembled so as to perform their usual function. Thus, a flanking control sequence operably-linked to a coding sequence may be capable of effecting the replication, transcription and/or translation of the coding sequence under conditions compatible with the control sequences. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a polypeptide or for an siRNA molecule will typically have its own operably-linked promoter sequence. The promoter can be a constitutive promoter, or an inducible promoter to allow selective transcription. Optionally, the promoter can be a cell-specific or tissue-specific promoter. Promoters can be chosen based on the cell-type or tissue-type that is targeted for delivery or treatment, for example.

The terms "polypeptide" and "protein" are used interchangeably herein and indicate a molecular chain of amino acids of any length linked through peptide bonds. Thus, peptides, oligopeptides, and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

The terms "transfection" and "transformation" are used interchangeably herein to refer to the insertion of an exogenous polynucleotide into a host, irrespective of the method used for the insertion, the molecular form of the polynucleotide that is inserted, or the nature of the host (e.g., prokaryotic or eukaryotic). The insertion of a polynucleotide per se and the insertion of a plasmid or vector comprised of the exogenous polynucleotide are included. The exogenous polynucleotide may be directly transcribed and, optionally, translated by the host (e.g., host organism or host cell), maintained as a nonintegrated vector, for example, a plasmid, or alternatively, may be stably integrated into the host genome. The terms "administration" and "treatment" are used herein interchangeably to refer to transfection of hosts in vitro or in vivo, using vectors of the present invention.

The term "wild-type" (WT), as used herein, refers to the typical, most common or conventional form as it occurs in nature.

Thus, the present invention includes methods of gene therapy whereby polynucleotides encoding the desired gene product are delivered to a subject, and the polynucleotide is transcribed and/or expressed in vivo. The term "gene therapy", as used herein, includes the transfer of genetic material (e.g., polynucleotides) of interest into a host to treat or prevent a genetic or acquired disease or condition phenotype, or to otherwise express the genetic material such that the encoded product is produced within the host. The genetic material of interest can encode a product (e.g., a polypeptide or functional RNA, such as siRNA) whose production in vivo is desired. For example, the genetic material of interest can encode a hormone, receptor, receptor ligand, enzyme, polypeptide or peptide of therapeutic value. For a review see, in general, the text "Gene Therapy" (*Advances in Pharmacology* 40, Academic Press, 1997). The genetic material may encode a product normally found within the species of the intended host, or within a different species. For example, if the polynucleotide encodes a cytokine, the cytokine may be the human cytokine, or that of another mammal, for example, regardless of the intended host. Preferably, polypeptides encoded by polynucleotides to be delivered and expressed in a host are normally found in the species of the intended host. Alternatively, the genetic material may encode a novel product. Another exemplified gene therapy method involves administering a vector of the invention, wherein one or more gene suppressing cassettes target and suppress a mutant (or otherwise dysfunctional) gene in the host, and wherein one or more gene promoting cassettes includes a polynucleotide encoding the correct wild-type gene and/or another desired gene to be expressed in the host.

Two basic approaches to gene therapy have evolved: (1) ex vivo and (2) in vivo gene therapy. The methods of the subject invention encompass either or both. In ex vivo gene therapy, host cells are removed from a patient and, while being cultured, are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient.

In in vivo gene therapy, target host cells are not removed from the subject, rather the gene to be transferred is introduced into the cells of the recipient organism in situ, that is within the recipient. Alternatively, if the host gene is defective, the gene is repaired in situ.

The vectors of the present invention are capable of delivery/transfer of heterologous nucleic acid sequences into a prokaryotic or eukaryotic host cell in vitro or in vivo. The vector may include elements to control targeting, expression and transcription of the nucleic acid sequence in a cell selective manner as is known in the art. It should be noted that often the 5'UTR and/or 3'UTR of the gene may be replaced by the 5'UTR and/or 3'UTR of other expression vehicles.

According to the methods of the present invention, the vectors are preferably administered to the host within a pharmaceutical composition that also includes a pharmaceutically acceptable carrier. Thus, the present invention includes pharmaceutical compositions comprising an effective amount of the vector of the invention and a pharmaceutically acceptable carrier. The pharmaceutical compositions of the subject invention can be formulated according to known methods for preparing pharmaceutically useful compositions. As used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils.

The pharmaceutically acceptable carrier can be one adapted for a particular route of administration. For example, if the vectors of the present invention are intended to be administered to the respiratory epithelium, a carrier appropriate for oral or intranasal administration can be used.

Formulations are described in a number of sources which are well known and readily available to those skilled in the art. For example, *Remington's Pharmaceutical Sciences* (Martin E. W., 1995, Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The vectors of the present invention can be conjugated with chitosan or chitosan derivatives. Such chitosan conjugates can be administered to hosts according to the methods of the present invention. For example, DNA chitosan nanospheres can be generated, as described by Roy, K. et al. (*Nat Med,* 1999, 5:387). Chitosan allows increased bioavailability of the nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue. In one embodiment of the present invention, the vectors are conjugated with chitosan-derived nanoparticles.

The present invention further includes method for producing a vector of the present invention by combining at least one polynucleotide encoding an siRNA molecule with an operably linked promoter sequence to form a gene suppressing cassette, as described herein; and, optionally combining at least one gene promoting cassette as described herein with the at least one suppressing cassette to form a vector. Combination of sequences can be carried out using methods known in the art, including various digestion and ligation steps, as exemplified herein.

The terms "comprising", "consisting of" and "consisting essentially of" are defined according to their standard meaning. The terms may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a vector" includes more than one such vector, a reference to "a polynucleotide" includes more than one such polynucleotide, a reference to "a polypeptide" includes more than one such polypeptide, a reference to "a host cell" includes more than one such host cell, a reference to an "siRNA molecule) include more than one such siRNA molecule, and the like.

Standard molecular biology techniques known in the art and not specifically described were generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989) and in Perbal, A Practical Guide to Molecular Cloning, John Wiley & Sons, New York (1988), and in Watson et al., Recombinant DNA, Scientific American Books, New York and in Birren et al. (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659; and 5,272,057; and incorporated herein by reference. Polymerase chain reaction (PCR) was carried out generally as in PCR Protocols: A Guide To Methods And Applications, Academic Press, San Diego, Calif. (1990). In situ (In-cell) PCR in combination with Flow Cytometry can be used for detection of cells containing specific DNA and mRNA sequences (Testoni et al., *Blood*, 1996, 87:3822.)

All patents, patent applications, provisional applications, and publications referred to or cited herein, whether supra or infra, are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Figure 1B:
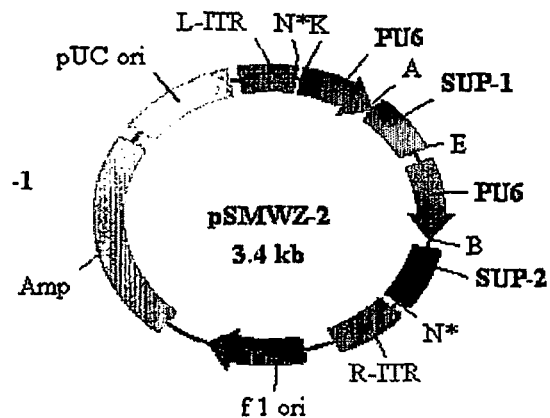
Figure 1C:
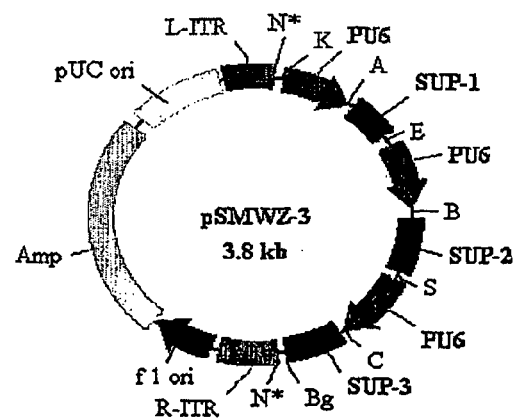
Figure 1D:
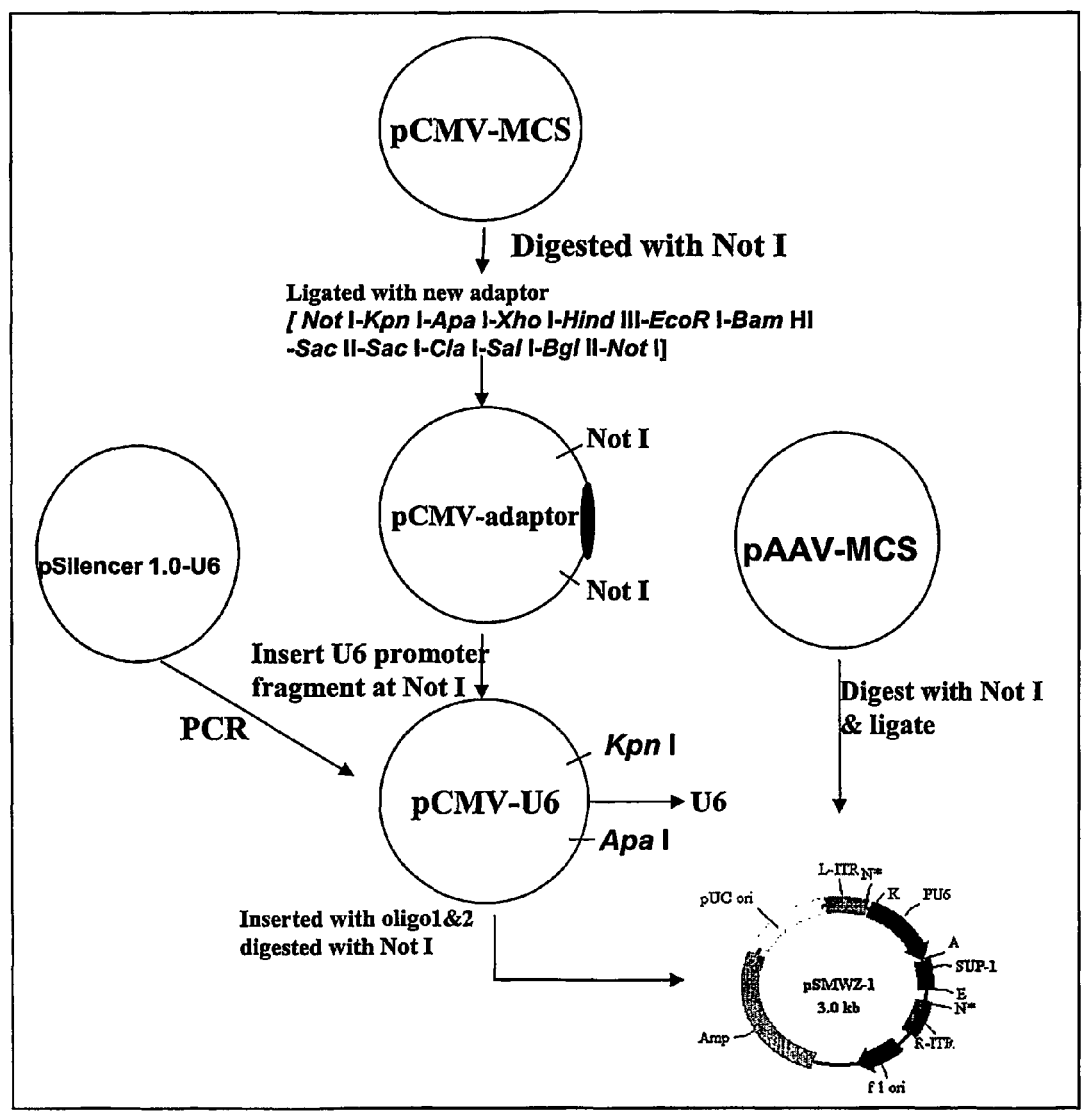
Figure 1E:
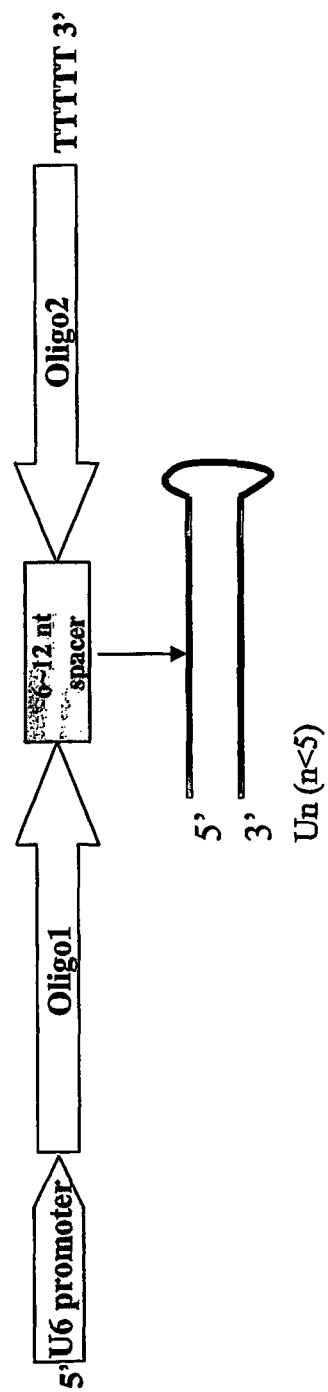
Figure 2A:
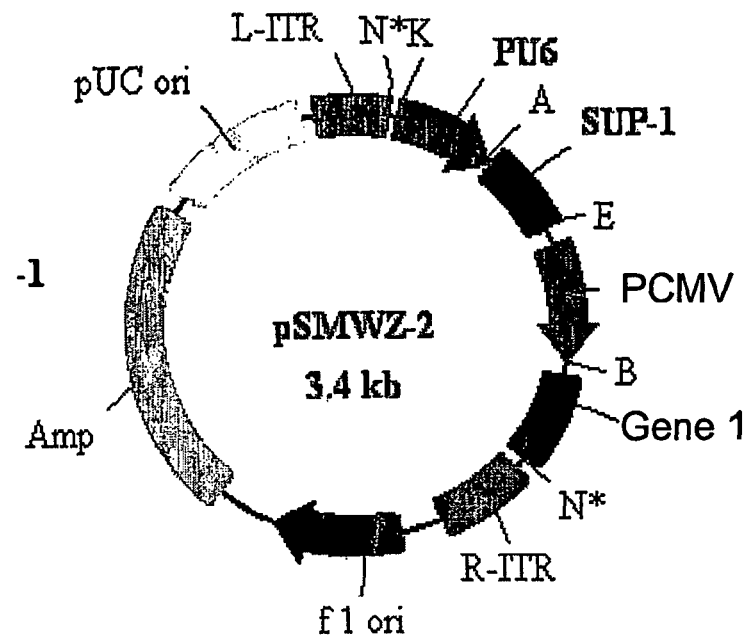
FIGS. 2A and 2B show that the vector in FIG. 1A can be modified to contain two cassettes, one gene promoting cassette containing a gene upregulated by the CMV promoter (PCMV) (as shown in FIG. 2A) or a tissue-specific promoter for lung, such as pulmonary surfactant protein B (PSPB) promoter (as shown in FIG. 2B) and a suppressor cassette (SUP1) (i.e., gene suppressing cassette). The gene promoting cassette can be cloned into the Not I site of the vector in FIG. 1A.
Figure 2B:
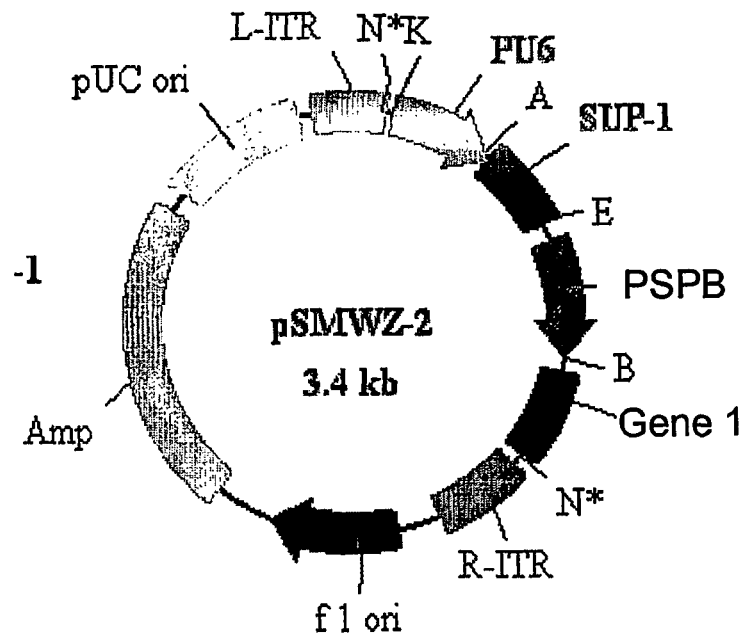
Figures 3A, 3B, 3C:
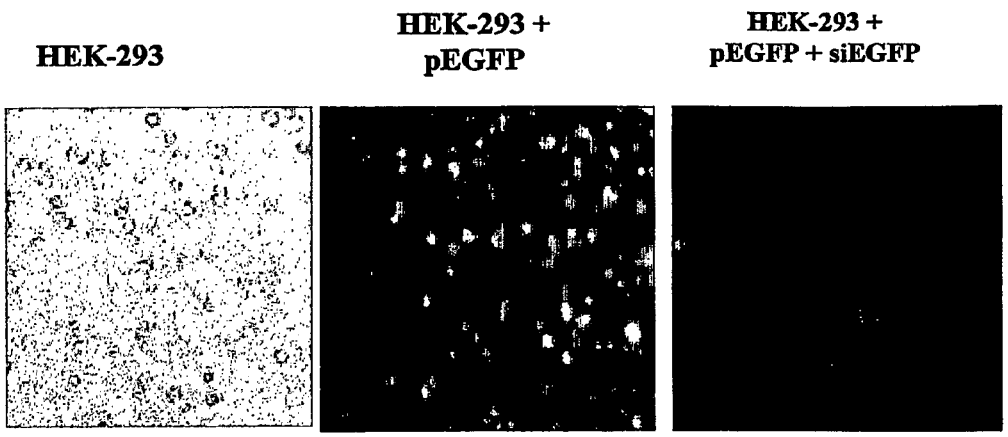
FIGS. 3A-3D show that Si-GFP inhibits expression of enhanced green fluorescent protein (EGFP) in cultured cells. To test the utility of the siRNA constructs, siRNA oligos specific for EGFP and the NS1 gene of human respiratory syncytial virus (RSV-NS1) (as control) genes, were cloned separately into the pSMWZ-1 plasmid (shown in FIGS. 1A-1C). To test the function of the pSMWZ-1 construct expressing siRNA specific for EGFP, $1 \times 10^5$ HEK293 cells were seeded into six-well tissue culture plates and incubated at 37°/5% $CO^2$ until the cells reached 50% confluency. Then cells were co-transfected with pVAX-EGFP and either pSMWZ-1-siEGFP or pSMWZ-1-RSV-siNS1 at different ratios (1:10, 0.3 µg: 3 µg; 1:20, 0.3 µg: 6 µg; and 1:40, 0.3 µg: 12 µg) using lipofectin reagent. After 48 hours of transfection, EGFP-positive cells were visualized using a fluorescence microscope and counted randomly from 15 different spots.
Figure 3D:
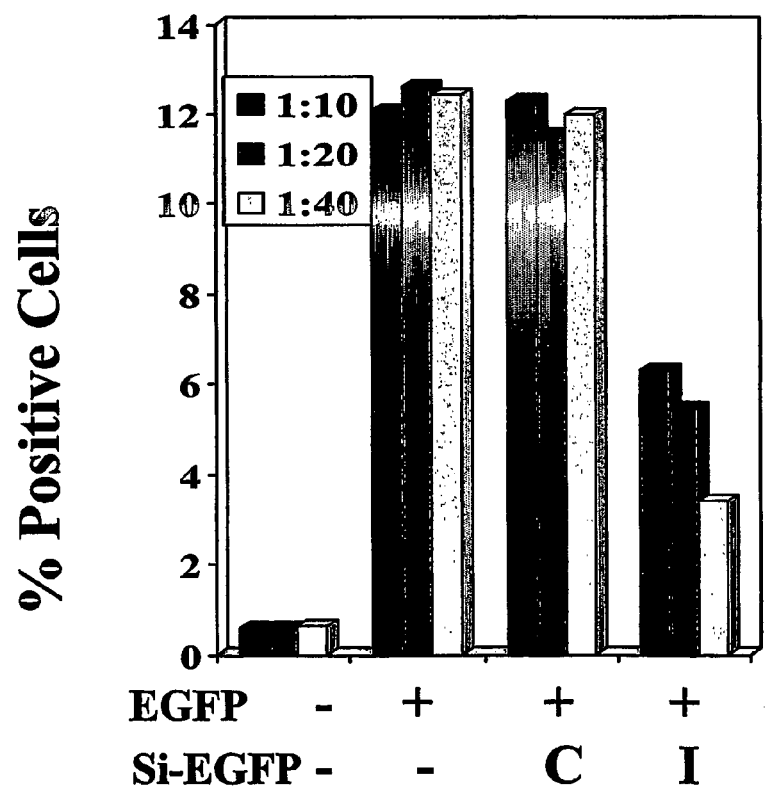

A Vector for Silencing Expression of Gene(s) Using Adeno-Associated Virus as Vector for Gene Delivery Plasmid vector pSMWZ-1 was created by the following steps: (i) the pCMV-MCS plasmid (STRATAGENE) was digested with Not I and the larger fragment, containing the ampicillin gene, was ligated to the synthetic adapter, containing, in order, Not I-Kpn I-Apa I-Xho I-Hind III-EcoR I-Bam HI-Sac II-Sac I-Cla I-Sal I-Bgl II-Not I; (ii) the suppressor cassette, containing the mouse U6 promoter linked to a multiple cloning site, was obtained by PCR amplification, using specific primers with the desired restriction sites from the template pSilencer 1.0-U6 (AMBION), and inserted in the adaptor at the appropriate sites; and (iii) the modified pCMV-MCS plasmid was digested with Not I and the smaller fragment was ligated to the 2.9 kb fragment of pAAV-MCS (STRATAGENE) obtained following its Not I digestion. Plasmids pSMWZ-2 and pSMWZ-3 were created by inserting additional suppressor cassettes at the NotI site. The map of the resulting plasmids is shown in FIGS. 1A-1C. A schematic diagram of a method for producing the plasmids is shown in FIG. 1D. A schematic diagram of a suppressor cassette is shown in FIG. 1E. HEK293 cells, which produce the adenovirus E1 genes in trans, will be cotransfected with recombinant pAAV vector, pRC and pHelper to produce recombinant AVV particles in these cells.

EXAMPLE 2

Promoting and/or Suppressing Multiple Gene Expression Using Adeno-Associated Virus as Vector To produce dual function AAV vectors that are capable of promoting expression of one or more genes, while simultaneously suppressing expression of one or more other genes, the promoting genes (p-genes) are directionally inserted into EcoR I and Xho I sites in the plasmid pCMV-MCS (STRATEGENE). The recombinant pCMV-MCS plasmid was then digested with Not I and the fragment containing target genes was isolated and ligated to the larger 2.9 kb fragment of pAAV-MCS after its digestion with Not I. Next, the recombinant AAV-MCS was redigested with BstE II and Rsr II, and the product was purified. Secondly, to further clone the suppressor cassettes, the pSilencer 1.0-U6 (AMBION) was digested with Kpn I and Bam HI, and the smaller fragment, harboring the U6 promoter and a few restriction endonuclease sites, were purified and ligated with the linkers BstE II-Kpn I and Bam HI-Rsr II at both ends. This fragment was then ligated with the product of rAAV-MCS fragment, digested with BstE II and Rsr II. To obtain the recombinant AAV with p-gene and suppressor cassette(s), HEK 293 are co-transfected with rAAV-MCS, AAV-RC and AAV-helper, and the recombinant viruses are purified, as per the manufacturer's instructions.

EXAMPLE 3

A Vector for Silencing Expression of Gene(s) Using Non-Viral Gene Delivery

To produce plasmid vectors capable of producing a gene suppressor, the plasmid pVAX-1 (INVITROGEN) was digested with Mlu I and Xcm I, and the purified fragment was ligated with an adaptor containing, in order: Mlu I-Kpn I-Apa I-Xho I-Hind III-EcoRI-Bam HI-Sac II-Pst I-Cla I-Sal I-Bag II-Not I-Xcm I. The U6 promoter was inserted into the pVAX vector by PCR amplification of the promoter using vector pSilencer 1.0-U6 (AMBION) as a template and specific primers with the appropriate restriction sites. The U6 promoter was inserted into the adaptor at the Kpn I/Apa I, EcoR I/BamH I and Cla I/Sal I sites, respectively, to construct the different vectors with a single or two or three U6 promoter(s). These vectors will allow cloning of the specific suppressor oligos encoding siRNA for the desired gene(s) cloned behind the U6 promoter(s) to silence the corresponding target genes.

EXAMPLE 4

A Vector for Regulating Gene Expression that Involves Promoting Expression of One or More Genes While Suppressing One or More of Other Genes To produce vectors that are capable of augmenting expression of desired gene(s) (referred to in the figures as "p-genes"), and suppressing expression of other genes (referred to in the figure as "SUP genes") with siRNA, first p-genes were directionally cloned into Hind III and Xho I sites in the plasmid pVAX-1 (INVITROGEN). Then, pSilencer 1.0-U6 (AMBION) was digested with Kpn I and EcoR I, and the smaller fragment harboring the U6 promoter was ligated to a synthetic adaptor containing Xcm I-Kpn I and EcoR I-BsaB I. Finally, the recombinant pVAX carrying p-gene(s) was digested with Xcm I and BsaB I and ligated with the U6 promoter containing fragment described above. In the resulting construct, specific suppressor oligos were inserted at the restriction enzyme sites (Sal L Cla I, EcoR V and EcoR I) to silence the target genes.

EXAMPLE 5

Testing of a Prototype Vector

To test the utility of the siRNA constructs, siRNA oligos specific for EGFP and the NS1 gene of human respiratory syncytial virus RSV-NS1) (as control) genes, were cloned separately into the pSMWZ-1 plasmid (pSMWZ-1 is shown in FIG. 1A). To test the function of the pSMWZ-1 construct expressing siRNA specific for EGFP, $1\times10^5$ HEK293 cells were seeded into six-well tissue culture plates and incubated at 37°/5% $CO^2$ until the cells reached 50% confluency. Then cells were co-transfected with pVAX-EGFP and either pSMWZ-1-siEGFP (I) or pSMWZ-1-RSV-siNS1 (C) at different ratios (1:10, 0.3 µg: 3 µg; 1:20, 0.3 µg: 6 µg; and 1:40, 0.3 µg: 12 µg) using lipofectin reagent. After 48 hours of transfection, EGFP-positive cells were visualized using a fluorescence microscope and counted randomly from 15 different spots (FIGS. 3A-3D). The results of these experiments demonstrate that siRNA oligos cloned in the pSMWZ-1 vector are capable of inhibiting specific gene expression in a dose-dependent manner. The RSV-siNS1 molecule (an oligo for inhibiting RSV NS1 gene expression in these HEK293 cells) was used as a control.

EXAMPLE 6

Figures 4A, 4B:
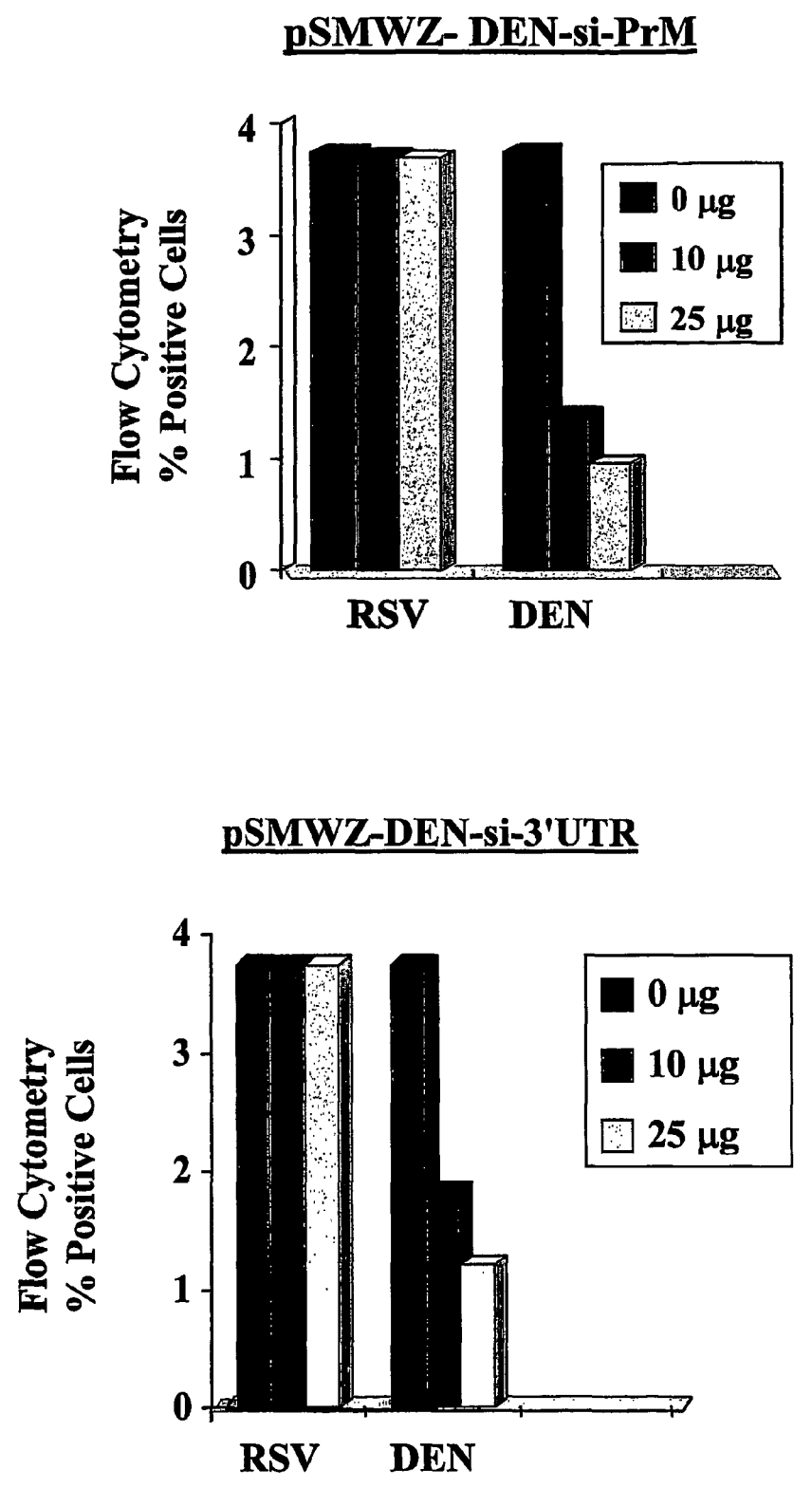

A Vector Expressing an siRNA Against DEN-2 Inhibits DEN-2 Infection of VERO Cells Two siRNA oligonucleotides (oligos) targeting the PRM gene of DEN-2 were cloned separately into pSMWZ-1. RSV-siNS1 oligo (as control) was cloned into pSMWZ-1. To test the function of pSMWZ-DEN-siPRM and pSMWZ-DEN-si3'UTR, $1\times10^5$ VERO cells were seeded into six-well tissue culture plates and incubated at 37°/5% $CO^2$ until the cells reached 50% confluency. Then cells were transfected with either pSMWZ-DEN-siPRM, pSMWZ-DEN-Si3'UTR, or pSMWZ-1-RSV-siNS1 (RSV) using 0, 10 or 25 mg of plasmid in lipofectin reagent. After 48 hours of transfection, cells were incubated with DEN-2 virus. The cells were then infected with DEN-2 virus (at multiplicity of infection of 0.1). Those cells infected with DEN-2 virus were identified by flow cytometry using an antibody to DEN-2 virus (MICROBIX BIOSYSTEMS INC, Clone No 3H5). Results are shown in FIGS. 4A and 4B. The results of these experiments demonstrate that Si-oligos specific for DEN-2 cloned in the pSMWZ-1 vector are capable of inhibiting DEN-2 viral infection in a dose-dependent manner. The RSV-siNS1 molecule (an oligo for inhibiting RSV NS1 gene expression) was used as a control.

EXAMPLE 7

AAV Expressing siRNA Targeted to the DV Genome Decreases DV Infection in VERO Cells Described herein is an adeno-associated virus (AAV) system capable of expressing siRNA cassettes. This vector has been tested with a siRNA cassette composed of a nucleotide sequence from the 3' UTR of the DV genome (DEN-si3'UTR), which is common to all four serotypes. As described in detail below, the results obtained in Vero cells infected with AAV-DEN-si3'UTR show significant decreases in DV infection.

Figure 5B:
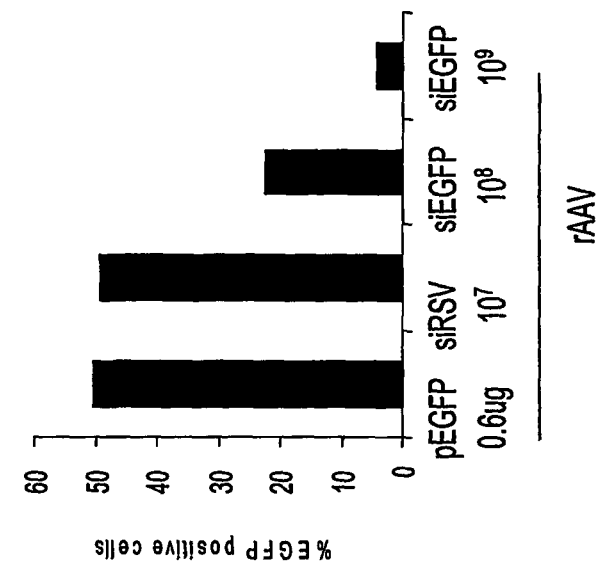
Figure 5A:
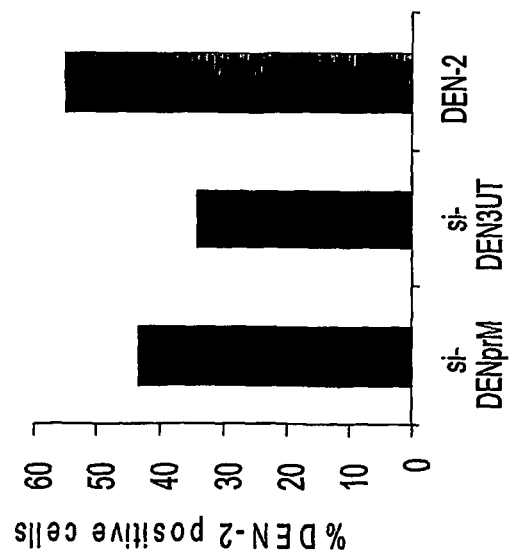
Figures 6A, 6B, 6C:
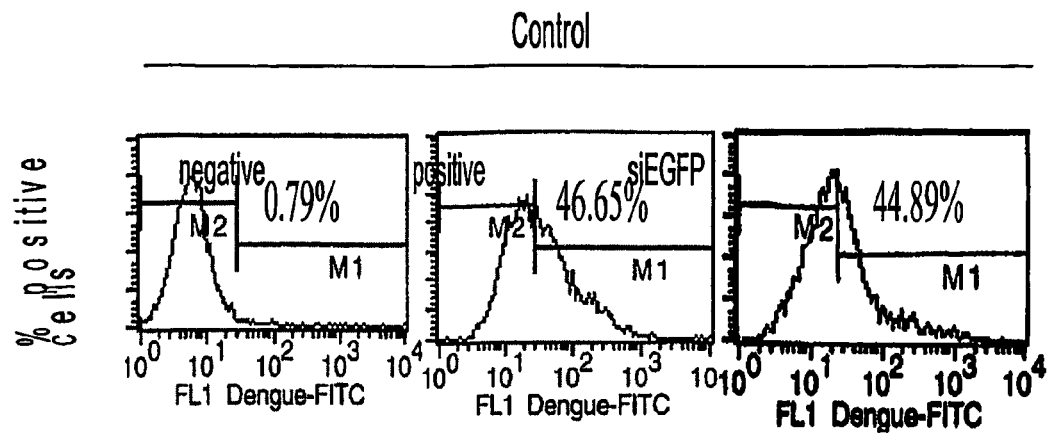
Figures 6D, 6E, 6F:
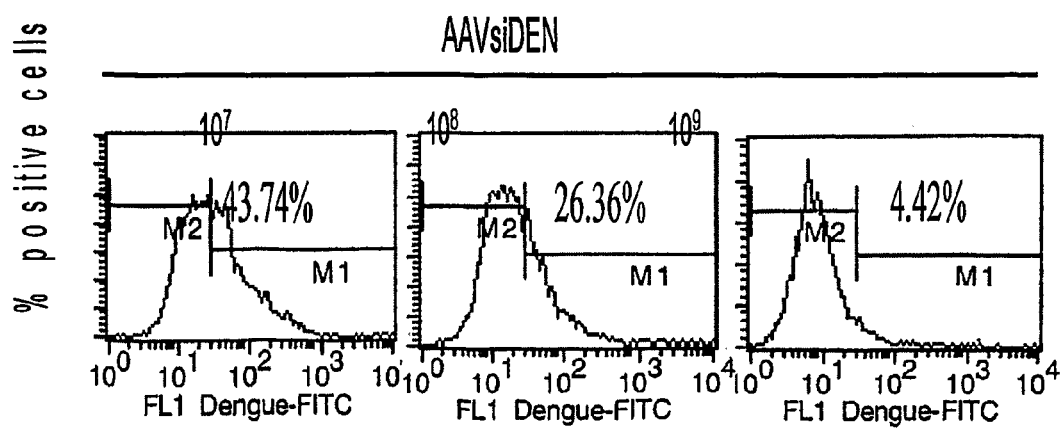
Figures 7A, 7B, 7C, 7D:
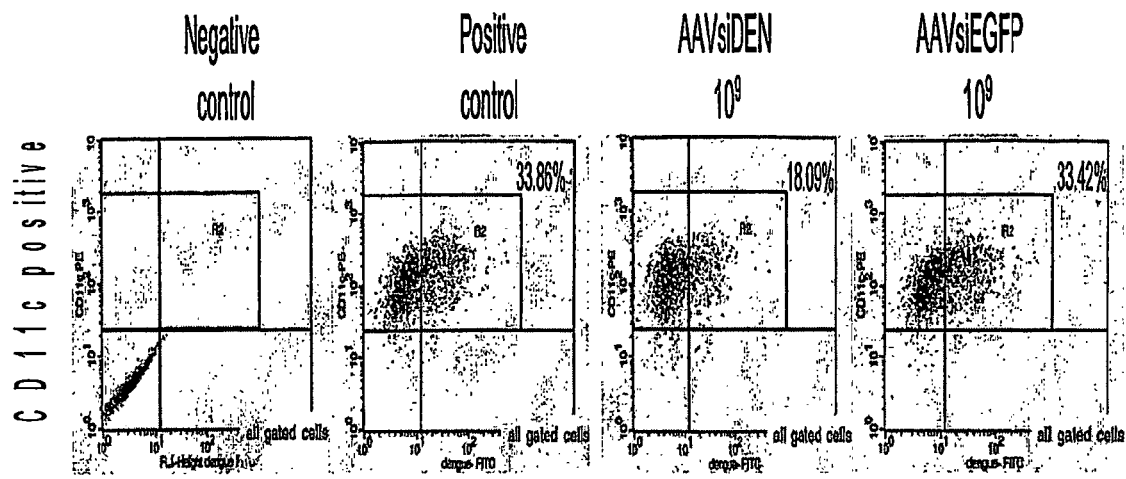
Figure 8:
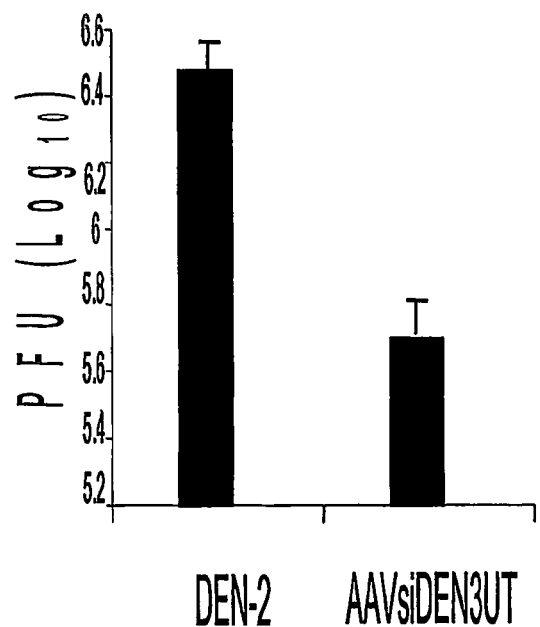
Figure 9:
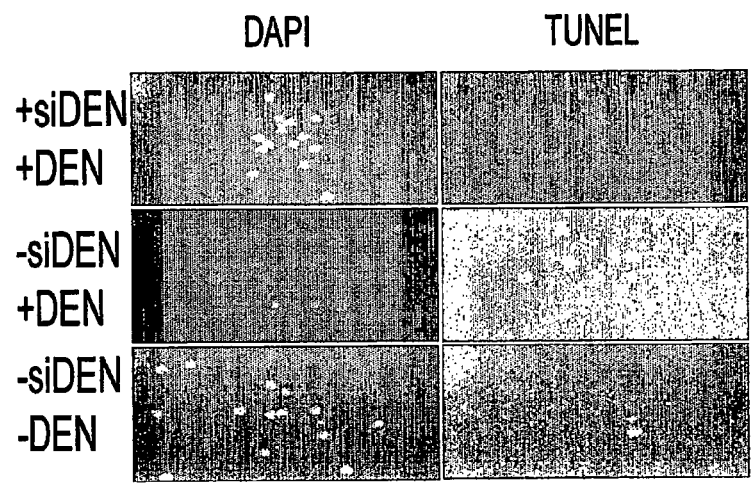
Figure 10:
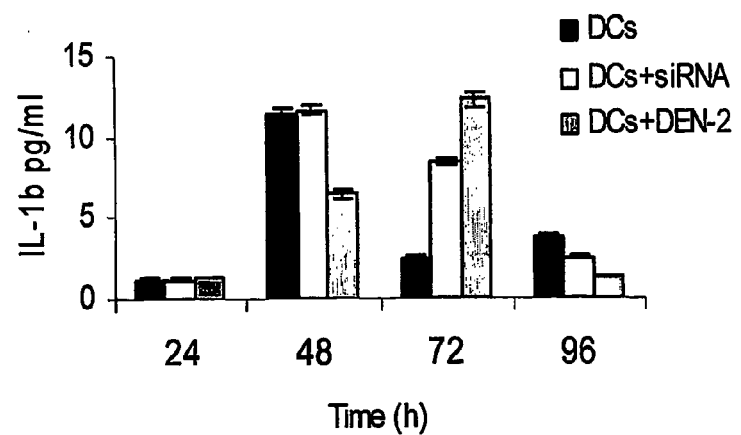

To test various siDEN candidates, Vero cells were transfected with either pSMWZ-siDENpreM (siDENpreM) or pSMWZ-siDEN3UT(siDEN3UT), then two days post-transfection infected with DEN-2 (strain 16803) at an MOI of 0.1. At five days post-infection, the numbers of DEN-2 virus infected cells were quantified by fluorescence microscopy using antibody to DEN-2 envelope protein and FITC-conjugated secondary antibody. The results showed that siDEN3UT was better than siDENpreM in suppression of DEN-2 infection (FIG. 5A).

The AAVsiRNA system was similarly tested using HEK293 cells which were infected with AAVsiEGFP and then transfected with pEGFP. The decrease in the percentage of cells expressing EGFP showed that there was a silencing of EGFP expression in a dose-dependent and sequence-specific manner (FIG. 5B).

The vectors pSMWZ-DEN-si3'UTR or pSMWZ-1-siEGFP (described in Example 6) were cotransfected with helper plasmid into HEK-293 cells to generate recombinant AAV. HEK293 cells were cultured with DMEM (CELLGRO) plus 10% FBS (CELLGRO) and cotransfected with pSMWZ-siDEN-si3'UTR, pHelper and pAAV-RC (STRATAGENE) by standard calcium phosphate transfection. Cells were harvested 48 hr post-transfection and the cell pellets were stored at −80° C. Cells were lysed by 5 cycles of freezing and thawing to release the virus. Crude viral lysate were collected by centrifugation at 27,000×g for 30 min, and the supernatants were harvested and put onto a CsCl gradient (density 1.20/1.50) in fresh tubes and centrifuged for 16 h at 100,000× g. Opalescent bands were collected post-ultracentrifugation. Titers of purified AAV-DEN-si3'UTR and AAV-siEGFP were measured using an AAV Titration ELISA Kit (PROGEN BIOTECHNIK, Germany).

To test the function of AAV-DEN-si3'UTR, $1\times10^5$ VERO cells were seeded into six-well tissue culture plates and infected with different dosages ($10^7$-$10^9$ PFU/ml) of AAV-DEN-si3'UTR or AAV-siEGFP (as control). After 2 days, the cells were infected with DEN-2 virus (strain 16803) at a multiplicity of infection (MOI) of 0.1. Five days later, those cells infected with DEN-2 virus were identified by flow cytometry using an antibody to DEN-2 virus (MICROBIX BIOSYSTEMS INC, Clone No 3H5). Cells pre-infected with AAV-DEN-si3'UTR, but not AAV-siEGFP, showed a significant reduction in DEN-2 infection, and the reduction was dose dependent (FIGS. 6A-6F).

EXAMPLE 8

AAV Expressing siRNA Targeted to the DV Genome Decreases DV Infection in Human Dendritic Cells (DCs)

DV is transmitted through *Aedes aegypti* mosquito bites, and resident skin dendritic cells (DCs) are regarded as the targets of DV infection (Marovich, M. et al. *J Investig Dermatol Symp Proc.*, 2001, 6:219). DCs are thought to be 10-fold more permissive for DEN infection than monocytes or macrophages (Wu, S. J. et al. *Nature Med*, 2000, 6:816). Described herein is an adeno-associated virus (AAV) system capable of expressing siRNA cassettes. This vector has been tested with a siRNA cassette composed of a nucleotide sequence from the 3' UTR of the DV genome (DEN-si3'UTR), which is common to all four serotypes. The results obtained in dendritic cells infected with AAV-DEN-si3'UTR show significant decreases in DV infection and DEN-induced apoptosis.

The ability of AAV-DEN-si3'UTR to attenuate DV infection was tested in human DCs. DCs were isolated from human blood and cultured in the presence of IL-4 and GM-CSF for 5 days to generate immature DCs (iDCs). These DCs were then infected with $10^9$ PFU/ml of recombinant AAV-DEN-si3'UTR or AAV-siEGFP (control). After 2 days the cells were infected with DEN-2 virus at an MOI of 0.1. Five days later, the numbers of DEN-2 infected cells were quantified by flow cytometry using DEN-2 antibody. Cells preinfected with AAV-DEN-si3'UTR showed a 50% reduction in the number of infected cells (FIGS. 7A-7D).

To test whether the reduction in the number of infected DCs involved a reduction in DEN titer, the culture supernatants were examined using a Vero cell-based plaque assay. AAV-mediated DEN-si3'UTR expression significantly decreased DEN-2 virus titer compared to control (FIG. 8). These results indicate that AAV-DEN-si3'UTR can significantly decrease DEN titers in human DCs.

EXAMPLE 9

Silencing DEN-2 Genes Inhibits Apoptosis in DCs

It has been reported that DV infection induces apoptosis of DCs (Ho, L. J. et al. *J Immunol,* 2001, 166:1499) leading to an immunosuppressed condition. To examine the effect of AAV-mediated siRNA delivery in DCs, apoptosis was investigated in infected DCs using the TUNEL assay. Infected DCs were harvested on day 5 of infection with DEN-2 virus. Aliquots of DCs were put onto slides using a cytospin and fixed with 4% paraformaldehyde. Apoptotic DCs were determined using the terminal dUTP nick end-labeling assay according to the instructions (TUNEL, Promega, Madison Wis.) and representative fields were visualized by fluorescence microscopy. The results showed that a small percentage of DCs undergo apoptosis naturally during culture, but DEN infection causes much more apoptosis. The AAVsiRNA-treated (AAV-DEN-si3'UTR-treated) DEN-infected DCs showed significantly fewer apoptotic cells compared to DEN-infected cells without AAVsiRNA (without AAV-DEN-si3'UTR), as shown in FIG. 9.

EXAMPLE 10

AAV-DEN-Si3'UTR Delivery Does Not Induce Acute Inflammation in DCs

The supernatants of infected DCs were collected at different time points and cytokines were measured using cytoline bead array (CBA) and ELISA assays. As shown in FIG. 10, cultured DCs spontaneously produced increased IL-1β (IL-1b). A variety of cytokines including IFN-γ, TNF-α, IL-8, IL-6, IL-12 were measured. In the presence of AAV-siRNA infection, the production of IFN-γ, TNF-α, IL-8, IL-6, and IL-12 did not change significantly compared with cultured DCs. IL-1b secretion at 72 h post-infection was increased, however. These results indicate that in this system, AAV-siRNA delivery does not induce acute inflammation in DCs in vitro.

The results described in the foregoing examples indicate that siRNAs may be used to attenuate DEN infection in human DCs and may have therapeutic value.

Interference of gene expression by siRNAs is a novel strategy to knock down specific genes in cells or tissues, and the specific silencing of pathogen genes using siRNA is a very attractive approach for the clinical treatment of infectious diseases. Long dsRNAs (of >30 nt in length) activate a dsRNA-dependent protein kinase and 2',5'-oligoadenylate synthetase in mammalian cells, which leads to a non-specific reduction in levels of mRNAs (Stark, G. R. et al. *Annu Rev Biochem,* 1998, 67:227-264). The endogenous expression of siRNAs from introduced DNA templates is thought to overcome some limitations of exogenous siRNA delivery, in particular its transient effects on silencing specific genes and loss of phenotype (Tusch, L. T. *Nature Biotechnol.,* 2002, 20:446-448). AAV vectors have been proven to be safe and efficacious in Phase I clinical trials for gene therapy of cystic fibrosis and hemophilia B and are regarded as a potential alternative to retroviral and adenoviral vectors for gene therapy in humans. The AAV vectors have a number of advantages over other vectors. They are not pathogenic and do not induce production of neutralizing antibodies that could reduce transgene function. They possess a broad-range of tissue tropism and the capability of inducing long-term transgene expression (Srivastava, A. *J Cell Biochem Suppl,* 2002, 38:39-45). In this study, the present inventors utilized a novel AAV system to deliver DEN siRNA into mammalian cells and estimated its anti-DEN effect in vitro. In this AAV system, the present inventors incorporated the mouse U6 promoter, which is important for transcription and folding of the suppressor RNA, into a plasmid pCMV-U6.

The choice of appropriate target genes is important for the success of the siRNA strategy, and two siRNAs derived from either the pre-M or the 3' NCR region of DEN-2 were used in the study described herein. An internal deletion of 3' NCR nucleotide sequences was found to be lethal for DEN virus replication in an in vivo study (Men, R. et al. *J. Virol.* 1996, 70:3930-3937). The 3' NCR of the flavivirus genome, which presumably functions as a promoter for minus-strand RNA synthesis, is predicted to form a stem-and-loop secondary structure. Computational analyses have revealed that there is conserved sequence in all flaviviruses within the 3' end (Proutski, V. et al. *Nucleic Acids Res,* 1997, 25:1194-1202; Rauscher, S. F et al. RNA, 1997, 3:779-791). Thus, two siRNA cassettes were tested in this study that included the 3'NCR sequence common to all four DEN serotypes. The other siRNA cassette is from the gene encoding the preM protein which is important for maturation of the virus into an infectious form. The test of anti-DEN efficiency showed that siDEN3UT attenuated DEN Infection better than siDEN-preM. Knocking down viral genes at the earlier stage of the viral multiplication cycle rather than in the structural protein synthesis phase may provide better antiviral protection, although the limited plasmid transfection ratio appeared to influence the suppression efficiency of siDEN to DEN-2 infection in Vero cells in the present study (FIG. 5A).

Immature DCs are the most permissive for DEN infection and serve as a source of DEN replication and production (Libraty, D. H. et al. *J Virol,* 2001, 75:3501-3508). Replication in the early target cells may be essential for dengue pathogenesis in the human host. In this study, the present inventors also utilized peripheral blood iDCs as a cell model to test the AAV system. Similar to results in Vero cells, AAV-mediated siDEN3UT delivery down-regulated DEN-2 protein expression in iDCs. However, the magnitude of suppression in iDCs at the same infectious titer of AAVsiDEN was less compared to that found in Vero cells. Previous data showed that variations in the efficiency of transduction among DCs derived from different normal blood donors is between 2% and 50% (Ponnazhagan, S. et al. *J Virol,* 2001, 75:9493-9501), and the present inventors found that the infectious ratio for AAVEGFP is about 45%~50% in Vero cells. That may be due to limited expression of the AAV receptor or differential activation of the mouse U6 promoter in Vero cells compared to DCs (Ilves, H. et al. *Gene,* 1996, 171:203-208). Increasing the AAV infection titer or utilizing a more effective promoter within the AAV vector backbone might elevate the suppression for DEN replication in iDCs. Nevertheless, DCs treated with recombinant AAV showed a significant reduction in DEN virus titer compared to control. This is important as viral titer is the gold standard for measuring antiviral activity.

DCs are one of the most powerful of APCs. After infection with virus in the periphery, iDCs process viral antigens, then differentiate into mature DCs and migrate from peripheral tissues to lymph nodes where they prime naïve CD4 and CD8 T lymphocytes to maintain protective antiviral cytotoxic T cell memory (Banchereau, J. and Steinman, R. M. *Nature,* 1998, 392:245-252; Ludewig, B. et al. *J Immunol,* 1999, 163:1839-1844). Thus, DCs play an important role in the initiation of antiviral immunity and provide a crucial step in the development of adaptive antiviral immunity. Previous data showed that DEN infection induces apoptosis of DCs (Ho, L. J. et al. *J Immunol,* 2001, 166:1499-1506), which leads to a state of temporary immune-suppression during DEN fever. An important observation in the study is that AAVsiDEN treatment resulted in a significant decrease in apoptotic iDCs. The attenuation of apoptosis in iDCs following AAV-mediated siRNA delivery suggests that AAVsiRNA may be immunologically protective. After the primary DEN infection, most patients appear viremic in the early febrile phase, but the viruses are quickly cleared from the blood system after defervescence (Vaughn, D. W. et al. *J Infect Dis,* 1997, 176:322-330). The activation of both a humoral and cellular immune response is considered to be involved in DEN clearance. The most severe outcome in DEN infection is development of DHF/DSS, which is associated with secondary infections by heterotypic DEN serotypes. It is postulated that the preexisting, cross-reactive, adaptive immune response leads to excessive cytokine production, complement activation, and the release of other inflammatory factors that produce DHF/DSS (Libraty, D. H. et al. *J Virol,* 2001, 75:3501-3508). Therefore, it should be imperative for prophylaxis of DHF/DSS to eliminate DEN infection by different serotypes in the early target cells. Attenuation of DEN infection in DCs and protection of infected DCs from apoptosis would be a benefit for the elimination of the early DEN infection and the development and maintenance of antiviral innate/adaptive immune response in vivo.

One of the important features of AAV vectors is the lack of inflammation following infection. The present inventors failed to detect significant IFNγ or IL-12 production in the supernatants of AAVsiDEN-infected DCs. This is in accordance with previous data (Bueler, H. et al. *Biol Chem,* 1999, 380:613-622; Kay, M. A. et al. *Nature Med,* 2001, 7:33-40; Zaiss, A. et al. *J Virol,* 2002, 76:4580-4590), which demonstrated that an AAV delivery system did not induce significant acute inflammatory responses and, therefore, is useful in gene therapy for DEN infection in humans.

In conclusion, the present inventors developed a novel AAV-mediated siRNA delivery system. The results demonstrate significant downregulation of DEN protein expression in Vero cells and human DCs, which strongly suggest that the AAV vector can be useful for siRNA delivery and that this AAV system may be applied in clinical settings to attenuate DEN infection, as well as other infections.

It should be understood that the examples and embodiments described herein are for illustrative purposes only and that various modifications or changes in light thereof will be suggested to persons skilled in the art and are to be included within the spirit and purview of this application.

SEQUENCE LISTING

```
<160> NUMBER OF SEQ ID NOS: 4

<210> SEQ ID NO 1
<211> LENGTH: 63
<212> TYPE: DNA
<213> ORGANISM: Artificial Sequence
<220> FEATURE:
<223> OTHER INFORMATION: oligonucleotide sequence encoding the siRNA
      targeting the EGFP gene (si-GFP)

<400> SEQUENCE: 1
ggcgatgcca cctacggcaa gcttctcgat tcgaagcttg ccgtaggtgg catcgccctt    60
ttt                                                                  63

<210> SEQ ID NO 2
<211> LENGTH: 62
<212> TYPE: DNA
<213> ORGANISM: Artificial Sequence
<220> FEATURE:
<223> OTHER INFORMATION: oligonucleotide sequence encoding the siRNA
      targeting the NS1 gene of RSV (RSV si-NS1):

<400> SEQUENCE: 2
ggcagcaatt cattgagtat gcttctcgaa ataagcatac tcaatgaatt gctgccttt     60 tg                                                                   62

<210> SEQ ID NO 3
<211> LENGTH: 65
```

```
<212> TYPE: DNA
<213> ORGANISM: Artificial Sequence
<220> FEATURE:
<223> OTHER INFORMATION: oligonucleotide sequence encoding the siRNA
      targeting the PRM gene of Dengue virus type 2 (DEN-si-PrM)

<400> SEQUENCE: 3
ggaagacata gattgttggt gcactcgagt caacgtgcac caacaatcta tgtcttccct    60
ttttg                                                                65

<210> SEQ ID NO 4
<211> LENGTH: 65
<212> TYPE: DNA
<213> ORGANISM: Artificial Sequence
<220> FEATURE:
<223> OTHER INFORMATION: oligonucleotide sequence encoding the siRNA
      targeting the 3' UTR of the PRM gene of Dengue virus type 2 (DEN-
      si-3'UTR)

<400> SEQUENCE: 4
ggaaaaacag catattgacg ctgctcgagt caacgcagcg tcaatatgct gttttteect    60 ttttg                                                                65
```

What is claimed is:

1. A method for attenuating Dengue virus (DV) infection in human cells susceptible to DV infection in vivo, said method comprising administering to the cells in vivo an effective amount of a vector comprising a gene suppressing cassette, wherein the gene suppressing cassette comprises a polynucleotide operably-linked to a promoter sequence, wherein the polynucleotide comprises the nucleotide sequence of SEQ ID NO:4, wherein the polynucleotide encodes a short interfering RNA (siRNA) molecule that targets a sequence within the 3' non-coding region of the DV genome that is common to four serotypes of DV, and wherein the polynucleotide is transcribed to produce the siRNA molecule.

2. The method of claim 1, wherein the vector is conjugated with chitosan.

3. The method of claim 1, wherein the vector is a non-viral vector.

4. The method of claim 1, wherein the vector is a viral vector.

5. The method of claim 1, wherein the vector is an adenoviral vector or adeno-associated viral vector.

6. The method of claim 1, wherein the vector is an adeno-associated viral vector.

7. The method of claim 1, wherein the siRNA molecule attenuates DV replication in the cells.

8. The method of claim 1, wherein the siRNA molecule has a hairpin structure.

* * * * *

UNITED STATES PATENT AND TRADEMARK OFFICE
CERTIFICATE OF CORRECTION

| | | |
|---|---|---|
| PATENT NO. | : 8,796,235 B2 | Page 1 of 1 |
| APPLICATION NO. | : 10/544146 | |
| DATED | : August 5, 2014 | |
| INVENTOR(S) | : Shyam S. Mohapatra and Weidong Zhang | |

It is certified that error appears in the above-identified patent and that said Letters Patent is hereby corrected as shown below:

In the Specification

Column 2,
Line 16, "(DBF/DSS)" should read --(DHF/DSS)--

Column 5,
Line 7, "(kSv)" should read --(RSV)--

Column 19,
Line 1, "(Sal L Cla I," should read --(Sal I, Cla I,--
Line 10, "RSV-NS1)" should read --(RSV-NS1)--

Signed and Sealed this
Tenth Day of March, 2015

Michelle K. Lee
*Deputy Director of the United States Patent and Trademark Office*